United States Patent [19]
Hirschberg et al.

[11] Patent Number: 5,935,808
[45] Date of Patent: Aug. 10, 1999

[54] CAROTENOID-PRODUCING BACTERIAL SPECIES AND PROCESS FOR PRODUCTION OF CAROTENOIDS USING SAME

[75] Inventors: Joseph Hirschberg; Mark Harker, both of Jerusalem, Israel

[73] Assignee: Yissum Research and Development Company of the Hebrew University of Jerusalem, Jerusalem, Israel

[21] Appl. No.: 08/902,518

[22] Filed: Jul. 29, 1997

[51] Int. Cl.[6] .................................................. C12P 23/00
[52] U.S. Cl. .......................................... 435/67; 435/252.1
[58] Field of Search .................................. 435/67, 252.1

[56] References Cited

U.S. PATENT DOCUMENTS

| | | | |
|---|---|---|---|
| 3,951,742 | 4/1976 | Shepherd et al. | 435/67 |
| 5,308,759 | 5/1994 | Gierhart | 435/67 |
| 5,591,343 | 1/1997 | Kitaoka et al. | 210/634 |
| 5,607,839 | 3/1997 | Tsubokura et al. | 435/67 |
| 5,648,264 | 7/1997 | Kume | 435/264 |

OTHER PUBLICATIONS

Matsuyama et al J.Gen. Microbiol. 1986. vol. 132 Part 4 pp. 865–875 Apr. 1986.

*Primary Examiner*—Herbert J. Lilling
*Attorney, Agent, or Firm*—Mark M. Friedman

[57] ABSTRACT

A novel Paracoccus species type strain DSM 11574 which produces and secretes carotenoids such as β-carotene, echinenone, β-cryptoxanthin, canthaxanthin, adonirubin, cis-adonixanthin, adonixanthin, astaxanthin and zeaxanthin in vesicles; carotenoid containing vesicles; and a process for production of carotenoids comprising (a) culturing a bacterial species in an nutrient medium including sources of carbon, nitrogen and inorganic substances; and (b) recovering an individual carotenoid pigment or a mixture of carotenoid pigments from the cells, vesicles and/or medium.

14 Claims, 7 Drawing Sheets

Fig. 2 Common pathway of early carotenoid reactions (detailed in Fig. 1)

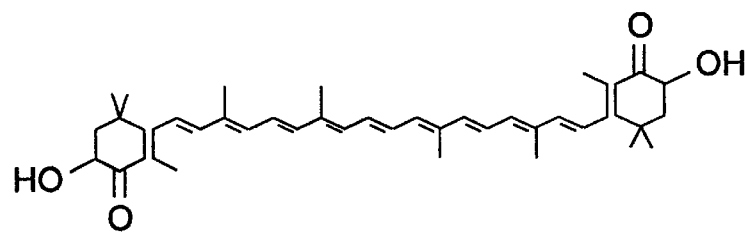
Astaxanthin
(3,3'-Dihydroxy-β,β-Carotene-4,4'-dione)
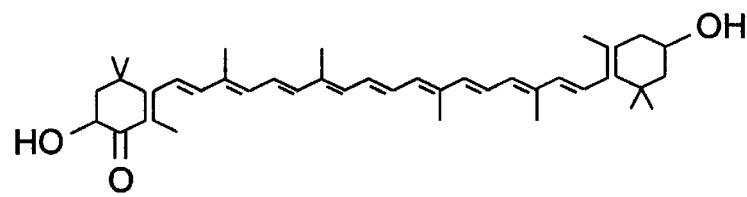
Adonixanthin
(3,3'-Dihydroxy-β,β-Carotene-4-one)
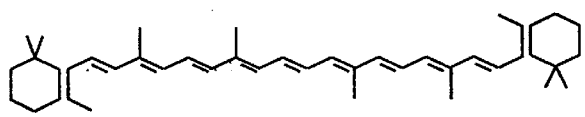
β-Carotene
(β,β-Carotene)
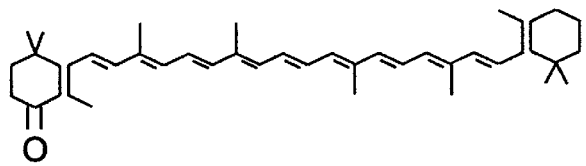
Echinenone
(β,β-Caroten-4 one)
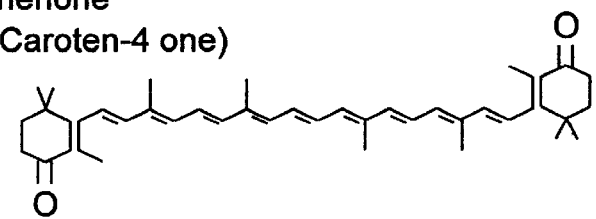
Canthaxanthin
(β,β-Caroten-4,4'-dione)
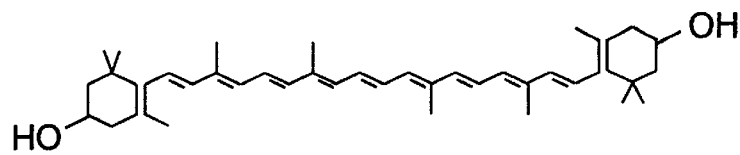
Zeaxanthin
((3R,3'R)-β,β-Carotene-3,3'-diol)
Fig. 3

CAROTENOID-PRODUCING BACTERIAL SPECIES AND PROCESS FOR PRODUCTION OF CAROTENOIDS USING SAME

FIELD AND BACKGROUND OF THE INVENTION

The present invention relates to a novel bacterial species. The novel species is most similar to the genus Paracoccus, as was determined by 16S ribosomal RNA analysis. However, the novel bacterial species produces and actively secretes carotenoid containing vesicles, during at least some stages of its life cycle, a phenomenon yet unseen, and therefore, the novel bacterial species, most likely, represents the first isolate of a new genus. The present invention further relates to a process for production of carotenoids, such as, but not limited to, β-carotene, echinenone, β-cryptoxanthin, canthaxanthin, adonirubin, cis-adonixanthin, adonixanthin, astaxanthin and zeaxanthin, using a species producing and secreting same.

The carotenoids of the present invention are natural pigments useful as feed additives, food additives, cosmetics, etc. As further detailed below, especially, astaxanthin is valuable from an industrial point of view as a feed additive, such as a color improver, for bred fishes such as salmon, trout, red sea bream etc., and as a safe natural food additive. In addition, adonixanthin is, if its industrial production process is established, promising as both food and feed additive as the astaxanthin is.

Further, β-carotene has been used as a food additive, feed additive, pharmaceutical substance, etc. Echinenone is promised as a food additive, feed additive, etc. Canthaxanthin has been used as a food additive, feed additive, in cosmetics etc. And zeaxanthin has been used as a food additive, feed additive, etc.

Carotenoids are natural pigments that are responsible for many of the yellow, orange and red colors seen in living organisms. Carotenoids are widely distributed in nature and have, in various living systems, two main biological functions. They serve as light-harvesting pigments in photosynthesis, and they protect against photooxidative damage. These and additional biological functions of carotenoids, their important industrial role, their biosynthesis and organisms producing them are discussed hereinbelow.

As part of the light-harvesting antenna, carotenoids can absorb photons and transfer the energy to chlorophyll, thus assisting in the harvesting of light in the range of 450–570 nm [see, Cogdell R. J. and Frank H. A. (1987) How carotenoids function in photosynthetic bacteria. Biochim Biophys Acta 895: 63–79; Cogdell R. (1988) The function of pigments in chloroplasts. In: Goodwin T. W. (ed) Plant Pigments, pp 183–255. Academic Press, London; Frank H. A., Violette C. A., Trautman J. K., Shreve A. P., Owens T. G. and Albrecht A. C. (1991) Carotenoids in photosynthesis: structure and photochemistry. Pure Appl Chem 63: 109–114; Frank H. A., Farhoosh R., Decoster B. and Christensen R. L. (1992) Molecular features that control the efficiency of carotenoid-to-chlorophyll energy transfer in photosynthesis. In: Murata N. (ed) Research in Photosynthesis, Vol I, pp 125–128. Kluwer, Dordrecht; and, Cogdell R. J. and Gardiner A. T. (1993) Functions of carotenoids in photosynthesis. Meth Enzymol 214: 185–193]. Although carotenoids are integral constituents of the protein-pigment complexes of the light-harvesting antennae in photosynthetic organisms, they are also important components of the photosynthetic reaction centers.

Most of the total carotenoids is located in the light harvesting complex II [Bassi R., Pineaw B., Dainese P. and Marquartt J. (1993) Carotenoid binding proteins of photosystem II. Eur J Biochem 212: 297–302]. The identities of the photosynthetically active carotenoproteins and their precise location in light-harvesting systems are not known. Carotenoids in photochemically active chlorophyll-protein complexes of the thermophilic cyanobacterium Synechococcus sp. were investigated by linear dichroism spectroscopy of oriented samples [see, Breton J. and Kato S. (1987) Orientation of the pigments in photosystem II: low-temperature linear-dichroism study of a core particle and of its chlorophyll-protein subunits isolated from Synechococcus sp. Biochim Biophys Acta 892: 99–107]. Those complexes contained mainly a β-carotene pool absorbing around 505 and 470 nm, which is oriented close to the membrane plane. In photochemically inactive chlorophyll-protein complexes, the β-carotene absorbs around 495 and 465 nm, and the molecules are oriented perpendicular to the membrane plane.

Evidence that carotenoids are associated with cyanobacterial photosystem (PS) II has been described [see, Suzuki R. and Fujita Y. (1977) Carotenoid photobleaching induced by the action of photosynthetic reaction center II: DCMU sensitivity. Plant Cell Physiol 18: 625–631; and, Newman P. J. and Sherman L. A. (1978) Isolation and characterization of photosystem I and II membrane particles from the blue-green alga *Synechococcus cedrorum*. Biochim Biophys Acta 503: 343–361]. There are two β-carotene molecules in the reaction center core of PS II [see, Ohno T., Satoh K. and Katoh S. (1986) Chemical composition of purified oxygen-evolving complexes from the thermophilic cyanobacterium Synechococcus sp. Biochim Biophys Acta 852: 1–8; Gounaris K., Chapman D. J. and Barber J. (1989) Isolation and characterization of a D1/D2/cytochrome b-559 complex from Synechocystis PCC6803. Biochim Biophys Acta 973: 296–301; and, Newell R. W., van Amerongen H, Barber J. and van Grondelle R. (1993) Spectroscopic characterization of the reaction center of photosystem II using polarized light: Evidence for β-carotene excitors in PS II reaction centers. Biochim Biophys Acta 1057: 232–238] whose exact function(s) is still obscure [reviewed by Satoh K. (1992) Structure and function of PS II reaction center. In: Murata N. (ed) Research in Photosynthesis, Vol. II, pp. 3–12. Kluwer, Dordrecht]. It was demonstrated that these two coupled β-carotene molecules protect chlorophyll P680 from photodamage in isolated PS II reaction centers [see, De Las Rivas J., Telfer A. and Barber J. (1993) 2-coupled β-carotene molecules protect P680 from photodamage in isolated PS II reaction centers. Biochim. Biophys. Acta 1142: 155–164], and this may be related to the protection against degradation of the D1 subunit of PS II [see, Sandmann G. (1993) Genes and enzymes involved in the desaturation reactions from phytoene to lycopene. (abstract), 10th International Symposium on Carotenoids, Trondheim CL1-2]. The light-harvesting pigments of a highly purified, oxygen-evolving PS II complex of the thermophilic cyanobacterium Synechococcus sp. consists of 50 chlorophyll a and 7 β-carotene, but no xanthophyll, molecules [see, Ohno T., Satoh K. and Katoh S. (1986) Chemical composition of purified oxygen-evolving complexes from the thermophilic cyanobacterium Synechococcus sp. Biochim Biophys Acta 852: 1–8]. β-carotene was shown to play a role in the assembly of an active PS II in green algae [see, Humbeck K., Romer S. and Senger H. (1989) Evidence for the essential role of carotenoids in the assembly of an active PS II. Planta 179: 242–250].

Isolated complexes of PS I from *Phormidium luridum*, which contained 40chlorophylls per P700, contained an average of 1.3 molecules of β-carotene [see, Thornber J. P., Alberte R. S., Hunter F. A., Shiozawa J. A. and Kan K. S. (1976) The organization of chlorophyll in the plant photosynthetic unit. Brookhaven Symp Biology 28: 132–148]. In a preparation of PS I particles from Synechococcus sp. strain PCC 6301, which contained 130±5 molecules of antenna chlorophylls per P700, 16 molecules of carotenoids were detected [see, Lundell D. J., Glazer A. N., Melis A. and Malkin R. (1985) Characterization of a cyanobacterial photosystem I complex. J Biol Chem 260: 646–654]. A substantial content of β-carotene and the xanthophylls cryptoxanthin and isocryptoxanthin were detected in PS I pigment-protein complexes of the thermophilic cyanobacterium *Synechococcus elongatus* [see, Coufal J., Hladik J. and Sofrova D. (1989) The carotenoid content of photosystem 1 pigment-protein complexes of the cyanobacterium *Synechococcus elongatus*. Photosynthetica 23: 603–616]. A subunit protein-complex structure of PS I from the thermophilic cyanobacterium Synechococcus sp., which consisted of four polypeptides (of 62, 60, 14 and 10 kDa), contained approximately 10 β-carotene molecules per P700 [see, Takahashi Y., Hirota K. and Katoh S. (1985) Multiple forms of P700-chlorophyll a-protein complexes from Synechococcus sp.: the iron, quinone and carotenoid contents. Photosynth Res 6: 183–192]. This carotenoid is exclusively bound to the large polypeptides which carry the functional and antenna chlorophyll a. The fluorescence excitation spectrum of these complexes suggested that β-carotene serves as an efficient antenna for PS I.

As mentioned, an additional essential function of carotenoids is to protect against photooxidation processes in the photosynthetic apparatus that are caused by the excited triplet state of chlorophyll. Carotenoid molecules with π-electron conjugation of nine or more carbon-carbon double bonds can absorb triplet-state energy from chlorophyll and thus prevent the formation of harmful singlet-state oxygen radicals. In Synechococcus sp. the triplet state of carotenoids was monitored in closed PS II centers and its rise kinetics of approximately 25 nanoseconds is attributed to energy transfer from chlorophyll triplets in the antenna [see, Schlodder E. and Brettel K. (1988) Primary charge separation in closed photosystem II with a lifetime of 11 nanoseconds. Flash-absorption spectroscopy with oxygen-evolving photosystem II complexes from Synechococcus. Biochem Biophys Acta 933: 22–34]. It is conceivable that this process, that has a lower yield compared to the yield of radical-pair formation, plays a role in protecting chlorophyll from damage due to over-excitation.

The protective role of carotenoids in vivo has been elucidated through the use of bleaching herbicides such as norflurazon that inhibit carotenoid biosynthesis in all organisms performing oxygenic photosynthesis [reviewed by Sandmann G. and Boger P. (1989) Inhibition of carotenoid biosynthesis by herbicides. In: Boger P. and Sandmann G. (Eds.) Target Sites of Herbicide Action, pp 25–44. CRC Press, Boca Raton, Fla.]. Treatment with norfilurazon in the light results in a decrease of both carotenoid and chlorophyll levels, while in the dark, chlorophyll levels are unaffected. Inhibition of photosynthetic efficiency in cells of *Oscillatoria agardhii* that were treated with the pyridinone herbicide, fluridone, was attributed to a decrease in the relative abundance of myxoxanthophyll, zeaxanthin and βcarotene, which in turn caused photooxidation of chlorophyll molecules [see, Canto de Loura I., Dubacq J. P. and Thomas J. C. (1987) The effects of nitrogen deficiency on pigments and lipids of cianobacteria. Plant Physiol 83: 838–843].

It has been demonstrated in plants that zeaxanthin is required to dissipate, in a nonradiative manner, the excess excitation energy of the antenna chlorophyll [see, Demmig-Adams B. (1990) Carotenoids and photoprotection in plants: a role for the xanthophyll zeaxanthin. Biochim Biophys Acta 1020: 1–24; and, Demmig-Adams B. and Adams W. W. III (1990) The carotenoid zeaxanthin and high-energy-state quenching of chlorophyll fluorescence. Photosynth Res 25: 187–197]. In algae and plants a light-induced deepoxidation of violaxanthin to yield zeaxanthin, is related to photoprotection processes [reviewed by Demmig-Adams B. and Adams W. W. III (1992) Photoprotection and other responses of plants to high light stress. Ann Rev Plant Physiol Plant Mol Biol 43: 599–626]. The light-induced deepoxidation of violaxanthin and the reverse reaction that takes place in the dark, are known as the "xanthophyll cycle" [see, Demmig-Adams B. and Adams W. W. III (1992) Photoprotection and other responses of plants to high light stress. Ann Rev Plant Physiol Plant Mol Biol 43: 599–626]. Cyanobacterial lichens, that do not contain any zeaxanthin and that probably are incapable of radiation energy dissipation, are sensitive to high light intensity; algal lichens that contain zeaxanthin are more resistant to high-light stress [see, Demmig-Adams B., Adams W. W. III, Green T. G. A., Czygan F. C. and Lange O. L. (1990) Differences in the susceptibility to light stress in two lichens forming a phycosymbiodeme, one partner possessing and one lacking the xanthophyll cycle. Oecologia 84: 451–456; Demmig-Adams B. and Adams W. W. III (1993) The xanthophyll cycle, protein turnover, and the high light tolerance of sun-acclimated leaves. Plant Physiol 103: 1413–1420; and, Demmig-Adams B. (1990) Carotenoids and photoprotection in plants: a role for the xanthophyll zeaxanthin. Biochim Biophys Acta 1020: 1–24]. In contrast to algae and plants, cyanobacteria do not have a xanthophyll cycle. However, they do contain ample quantities of zeaxanthin and other xanthophylls that can support photoprotection of chlorophyll.

Several other functions have been ascribed to carotenoids. The possibility that carotenoids protect against damaging species generated by near ultra-violet (UV) irradiation is suggested by results describing the accumulation of β-carotene in a UV-resistant mutant of the cyanobacterium *Gloeocapsa alpicola* [see, Buckley C. E. and Houghton J. A. (1976) A study of the effects of near UV radiation on the pigmentation of the blue-green alga *Gloeocapsa alpicola*. Arch Microbiol 107: 93–97]. This has been demonstrated more elegantly in *Escherichia coli* against phototoxic produce carotenoids [see, Tuveson R. W. and Sandmann G. (1993) Protection by cloned carotenoid genes expressed in *Escherichia coli* against phototoxic molecules activated by near-ultraviolet light. Meth Enzymol 214: 323–330]. Due to their ability to quench oxygen radical species, carotenoids are efficient antioxidants and thereby protect cells from oxidative damage. This function of carotenoids is important in virtually all organisms [see, Krinsky N. I. (1989) Antioxidant functions of carotenoids. Free Radical Biol Med 7: 617–635; and, Palozza P. and Krinsky N. I. (1992) Antioxidant effects of carotenoids in vivo and in vitro—an overview. Meth Enzymol 213: 403–420]. Other cellular functions could be affected by carotenoids, even if indirectly.

Although carotenoids in cyanobacteria are not the major photoreceptors for phototaxis, an influence of carotenoids on phototactic reactions, that have been observed in *Anabaena variabilis*, was attributed to the removal of singlet oxygen radicals that may act as signal intermediates in this system [see, Nultsch W. and Schuchart H. (1985) A model of the phototactic reaction chain of cyanobacterium *Anabaena variabilis*. Arch Microbiol 142: 180–184].

In flowers and fruits carotenoids facilitate the attraction of pollinators and dispersal of seeds. This latter aspect is strongly associated with agriculture. The type and degree of pigmentation in fruits and flowers are among the most important traits of many crops. This is mainly since the colors of these products often determine their appeal to the consumers and thus can increase their market worth.

Carotenoids have important commercial uses as coloring agents in the food industry since they are non-toxic [see, Bauernfeind J. C. (1981) Carotenoids as colorants and vitamin A precursors. Academic Press, London]. The red color of the tomato fruit is provided by lycopene which accumulates during fruit ripening in chromoplasts. Tomato extracts, which contain high content (over 80% dry weight) of lycopene, are commercially produced worldwide for industrial use as food colorant. Furthermore, the flesh, feathers or eggs of fish and birds assume the color of the dietary carotenoid provided, and thus carotenoids are frequently used in dietary additives for poultry and in aquaculture. Certain cyanobacterial species for example Spirulina sp. [see, Sommer T. R., Potts W. T. and Morrissy N. M. (1990) Recent progress in processed microalgae in aquaculture. Hydrobiologia 204/205: 435–443], are cultivated in aquaculture for the production of animal and human food supplements. Consequently, the content of carotenoids, primarily of β-carotene, in these cyanobacteria has a major commercial implication in biotechnology.

Most carotenoids are composed of a $C_{40}$ hydrocarbon backbone, constructed from eight $C_5$ isoprenoid units and contain a series of conjugated double bonds. Carotenes do not contain oxygen atoms and are either linear or cyclized molecules containing one or two end rings. Xanthophylls are oxygenated derivatives of carotenes. Various glycosilated carotenoids and carotenoid esters have been identified. The $C_{40}$ backbone can be further extended to give $C_{45}$ or $C_{50}$ carotenoids, or shortened yielding apocarotenoids. Some nonphotosynthetic bacteria also synthesize $C_{30}$ carotenoids. General background on carotenoids can be found in Goodwin T. W. (1980) The Biochemistry of the Carotenoids, Vol. 1, 2nd Ed. Chapman and Hall, New York; and in Goodwin T. W. and Britton G. (1988) Distribution and analysis of carotenoids. In: Goodwin T. W. (ed) Plant Pigments, pp 62–132. Academic Press, New York.

More than 640 different naturally-occurring carotenoids have been so far characterized, hence, carotenoids are responsible for most of the various shades of yellow, orange and red found in microorganisms, fungi, algae, plants and animals. Carotenoids are synthesized by all photosynthetic organisms as well as several nonphotosynthetic bacteria and fungi, however they are also widely distributed through feeding throughout the animal kingdom.

Carotenoids are synthesized de novo from isoprenoid precursors only in photosynthetic organisms and some microorganisms, they typically accumulate in protein complexes in the photosynthetic membrane, in the cell membrane and in the cell wall.

As detailed in FIG. 1, in the biosynthesis pathway of β-carotene, four enzymes convert geranylgeranyl pyrophosphate of the central isoprenoid pathway to β-carotene. Carotenoids are produced from the general isoprenoid biosynthetic pathway. While this pathway has been known for several decades, only recently, and mainly through the use of genetics and molecular biology, have some of the molecular mechanisms involved in carotenoids biogenesis, been elucidated. This is due to the fact that most of the enzymes which take part in the conversion of phytoene to carotenes and xanthophylls are labile, membrane-associated proteins that lose activity upon solubilization [see, Beyer P., Weiss G. and Kleinig H. (1985) Solubilization and reconstitution of the membrane-bound carotenogenic enzymes from daffodile chromoplasts. Eur J Biochem 153: 341–346; and, Bramley P. M. (1985) The in vitro biosynthesis of carotenoids. Adv Lipid Res 21: 243–279].

However, solubilization of carotenogenic enzymes from Synechocystis sp. strain PCC 6714 that retain partial activity has been reported [see, Bramley P. M. and Sandmann G. (1987) Solubilization of carotenogenic enzyme of Aphanocapsa. Phytochem 26: 1935–1939].

There is no genuine in vitro system for carotenoid biosynthesis which enables a direct essay of enzymatic activities. A cell-free carotenogenic system has been developed [see, Clarke I. E., Sandmann G., Bramley P. M. and Boger P. (1982) Carotene biosynthesis with isolated photosynthetic membranes. FEBS Lett 140: 203–206] and adapted for cyanobacteria [see, Sandmann G. and Bramley P. M. (1985) Carotenoid biosynthesis by Aphanocapsa homogenates coupled to a phytoene-generating system from *Phycomyces blakesleeanus*. Planta 164: 259–263; and, Bramley P. M. and Sandmann G. (1985) In vitro and in vivo biosynthesis of xanthophylls by the cyanobacterium Aphanocapsa. Phytochem 24: 2919–2922].

Reconstitution of phytoene desaturase from Synechococcus sp. strain PCC 7942 in liposomes was achieved following purification of the polypeptide, that had been expressed in *Escherichia coli* [see, Fraser P. D., Linden H. and Sandmann G. (1993) Purification and reactivation of recombinant Synechococcus phytoene desaturase from an overexpressing strain of *Escherichia coli*. Biochem J 291: 687–692].

Referring again to FIG. 1, carotenoids are synthesized from isoprenoid precursors. The central pathway of isoprenoid biosynthesis may be viewed as beginning with the conversion of acetyl-CoA to mevalonic acid. $D^3$-isopentenyl pyrophosphate (IPP), a $C_5$ molecule, is formed from mevalonate and is the building block for all long-chain isoprenoids. Following isomerization of IPP to dimethylallyl pyrophosphate (DMAPP), three additional molecules of IPP are combined to yield the $C_{20}$ molecule, geranylgeranyl pyrophosphate (GGPP). These 1'-4 condensation reactions are catalyzed by prenyl transferases [see, Kleinig H. (1989) The role of plastids in isoprenoid biosynthesis. Ann Rev Plant Physiol Plant Mol Biol 40: 39–59]. There is evidence in plants that the same enzyme, GGPP synthase, carries out all the reactions from DMAPP to GGPP [see, Dogbo O. and Camara B. (1987) Purification of isopentenyl pyrophosphate isomerase and geranylgeranyl pyrophosphate synthase from Capsicum chromoplasts by affinity chromatography. Biochim Biophys Acta 920: 140–148; and, Laferriere A. and Beyer P. (1991) Purification of geranylgeranyl diphosphate synthase from *Sinapis alba* etioplasts. Biochim Biophys Acta 216: 156–163].

The first step that is specific for carotenoid biosynthesis is the head-to-head condensation of two molecules of GGPP to produce prephytoene pyrophosphate (PPPP). Following removal of the pyrophosphate, GGPP is converted to 15-cis-phytoene, a colorless $C_{40}$ hydrocarbon molecule. This two-step reaction is catalyzed by the soluble enzyme, phytoene synthase, an enzyme encoded by a single gene (crtB), in both cyanobacteria and plants [see, Chamovitz D., Misawa N., Sandmann G. and Hirschberg J. (1992) Molecular cloning and expression in *Escherichia coli* of a cyanobacterial gene coding for phytoene synthase, a carotenoid biosynthesis enzyme. FEBS Lett 296: 305–310; Ray J. A., Bird C. R., Maunders M., Grierson D. and Schuch W. (1987) Sequence of pTOM5, a ripening related cDNA from tomato. Nucl Acids Res 15: 10587–10588; Camara B. (1993) Plant phy—toene synthase complex—component 3 enzymes, immunology, and biogenesis. Meth Enzymol 214: 352–365]. All the subsequent steps in the pathway occur in membranes. Four desaturation (dehydrogenation) reactions convert phytoene to lycopene via phytofluene, ζ-carotene, and neurosporene. Each desaturation increases the number of conjugated double bonds by two such that the number of conjugated double bonds increases from three in phytoene to eleven in lycopene.

Relatively little is known about the molecular mechanism of the enzymatic dehydrogenation of phytoene [see, Jones B. L. and Porter J. W. (1986) Biosynthesis of carotenes in higher plants. CRC Crit Rev Plant Sci 3: 295–324; and, Beyer P., Mayer M. and Kleinig H. (1989) Molecular oxygen and the state of geometric iosomerism of intermediates are essential in the carotene desaturation and cyclization reactions in daffodil chromoplasts. Eur J Biochem 184: 141–150]. It has been established that in cyanobacteria, algae and plants the first two desaturations, from 15-cis-phytoene to ζ-carotene, are catalyzed by a single membrane-bound enzyme, phytoene desaturase [see, Jones B. L. and Porter J. W. (1986) Biosynthesis of carotenes in higher plants. CRC Crit Rev Plant Sci 3: 295–324; and, Beyer P., Mayer M. and Kleinig H. (1989) Molecular oxygen and the state of geometric iosomerism of intermediates are essential in the carotene desaturation and cyclization reactions in daffodil chromoplasts. Eur J Biochem 184: 141–150]. Since the ζ-carotene product is mostly in the all-trans configuration, a cis-trans isomerization is presumed at this desaturation step. The primary structure of the phytoene desaturase polypeptide in cyanobacteria is conserved (over 65% identical residues) with that of algae and plants [see, Pecker I., Chamovitz D., Linden H., Sandmann G. and Hirschberg J. (1992) A single polypeptide catalyzing the conversion of phytoene to ζ-carotene is transcriptionally regulated during tomato fruit ripening. Proc Natl Acad Sci USA 89: 4962–4966; Pecker I. Chamovitz D., Mann V., Sandmann G., Boger P. and Hirschberg J. (1993) Molecular characterization of carotenoid biosynthesis in plants: the phytoene desaturase gene in tomato. In: Murata N. (ed) Research in Photosynthesis, Vol III, pp 11–18. Kluwer, Dordrectht]. Moreover, the same inhibitors block phytoene desaturase in the two systems [see, Sandmann G. and Boger P. (1989) Inhibition of carotenoid biosynthesis by herbicides. In: Boger P. and Sandmann G. (eds) Target Sites of Herbicide Action, pp 25–44. CRC Press, Boca Raton, Fla.]. Consequently, it is very likely that the enzymes catalyzing the desaturation of phytoene and phytofluene in cyanobacteria and plants have similar biochemical and molecular properties, that are distinct from those of phytoene desaturases in other microorganisms. One such a difference is that phytoene desaturases from *Rhodobacter capsulatus*, Erwinia sp. or fungi convert phytoene to neurosporene, lycopene, or 3,4-dehydrolycopene, respectively.

Desaturation of phytoene in daffodil chromoplasts [see, Beyer P., Mayer M. and Kleinig H. (1989) Molecular oxygen and the state of geometric iosomerism of intermediates are essential in the carotene desaturation and cyclization reactions in daffodil chromoplasts. Eur J Biochem 184: 141–150], as well as in a cell free system of Synechococcus sp. strain PCC 7942 [see, Sandmann G. and Kowalczyk S. (1989) In vitro carotenogenesis and characterization of the phytoene desaturase reaction in Anacystis. Biochem Biophys Res Com 163: 916–921], is dependent on molecular oxygen as a possible final electron acceptor, although oxygen is not directly involved in this reaction. A mechanism of dehydrogenase-electron transferase was supported in cyanobacteria over dehydrogenation mechanism of dehydrogenase-monooxygenase [see, Sandmann G. and Kowalczyk S. (1989) In vitro carotenogenesis and characterization of the phytoene desaturase reaction in Anacystis. Biochem Biophys Res Com 163: 916–921]. A conserved FAD-binding motif exists in all phytoene desaturases whose primary structures have been analyzed [see, Pecker I., Chamovitz D., Linden H., Sandmann G. and Hirschberg J. (1992) A single polypeptide catalyzing the conversion of phytoene to ζ-carotene is transcriptionally regulated during tomato fruit ripening. Proc Natl Acad Sci USA 89: 4962–4966; Pecker I., Chamovitz D., Mann V., Sandmann G., Boger P. and Hirschberg J. (1993) Molecular characterization of carotenoid biosynthesis in plants: the phytoene desaturase gene in tomato. In: Murata N. (ed) Research in Photosynthesis, Vol III, pp 11–18. Kluwer, Dordrectht]. The phytoene desaturase enzyme in pepper was shown to contain a protein-bound FAD [see, Hugueney P., Romer S., Kuntz M. and Camara B. (1992) Characterization and molecular cloning of a flavoprotein catalyzing the synthesis of phytofluene and ζ-carotene in Capsicum chromoplasts. Eur J Biochem 209: 399–407]. Since phytoene desaturase is located in the membrane, an additional, soluble redox component is predicted. This hypothetical component could employ $NAD(P)^+$, as suggested [see, Mayer M. P., Nievelstein V. and Beyer P. (1992) Purification and characterization of a NADPH dependent oxidoreductase from chromoplasts of *Narcissus pseudonarcissus*—a redox-mediator possibly involved in carotene desaturation. Plant Physiol Biochem 30: 389–398] or another electron and hydrogen carrier, such as a quinone. The cellular location of phytoene desaturase in Synechocystis sp. strain PCC 6714 and *Anabaena variabilis* strain ATCC 29413 was determined with specific antibodies to be mainly (85%) in the photosynthetic thylakoid membranes [see, Serrano A., Gimenez P., Schmidt A. and Sandmann G. (1990) Immunocytochemical localization and functional determination of phytoene desaturase in photoautotrophic prokaryotes. J Gen Microbiol 136: 2465–2469].

In cyanobacteria algae and plants ζ-carotene is converted to lycopene via neurosporene. Very little is known about the enzymatic mechanism, which is predicted to be carried out by a single enzyme [see, Linden H., Vioque A. and Sandmann G. (1993) Isolation of a carotenoid biosynthesis gene coding for ζcarotene desaturase from Anabaena PCC 7120 by heterologous complementation. FEMS Microbiol Lett 106: 99–104]. The deduced amino acid sequence of ζ-carotene desaturase in Anabaena sp. strain PCC 7120 contains a dinucleotide-binding motif that is similar to the one found in phytoene desaturase.

Two cyclization reactions convert lycopene to β-carotene. Evidence has been obtained that in Synechococcus sp. strain PCC 7942 [see, Cunningham F. X. Jr, Chamovitz D., Misawa N., Gantt E. and Hirschberg J. (1993) Cloning and functional expression in *Escherichia coli* of a cyanobacterial gene for lycopene cyclase, the enzyme that catalyzes the biosynthesis of β-carotene. FEBS Lett 328: 130–138], as well as in plants [see, Camara B. and Dogbo O. (1986) Demonstration and solubilization of lycopene cyclase from Capsicum chromoplast membranes. Plant Physiol 80: 172–184], these two cyclizations are catalyzed by a single enzyme, lycopene cyclase. This membrane-bound enzyme is inhibited by the triethylamine compounds, CPTA and MPTA [see, Sandmann G. and Boger P. (1989) Inhibition of carotenoid biosynthesis by herbicides. In: Boger P. and Sandmann G. (eds) Target Sites of Herbicide Action, pp 25–44. CRC Press, Boca Raton, Fla.]. Cyanobacteria carry out only the β-cyclization and therefore do not contain ε-carotene, δ-carotene and α-carotene and their oxygenated derivatives. The β-ring is formed through the formation of a "carbonium ion" intermediate when the C-1,2 double bond at the end of the linear lycopene molecule is folded into the position of the C-5,6 double bond, followed by a loss of a proton from C-6. No cyclic carotene has been reported in which the 7,8 bond is not a double bond. Therefore, full desaturation as in lycopene, or desaturation of at least half-molecule as in neurosporene, is essential for the reaction. Cyclization of lycopene involves a dehydrogenation reaction that does not require oxygen. The cofactor for this reaction is unknown. A dinucleotide-binding domain was found in the lycopene cyclase polypeptide of Synechococcus sp. strain PCC 7942, implicating NAD(P) or FAD as coenzymes with lycopene cyclase.

The addition of various oxygen-containing side groups, such as hydroxy-, methoxy-, oxo-, epoxy-, aldehyde or carboxylic acid moieties, form the various xanthophyll species. Little is known about the formation of xanthophylls. Hydroxylation of β-carotene requires molecular oxygen in a mixed-function oxidase reaction.

Clusters of genes encoding the enzymes for the entire pathway have been cloned from the purple photosynthetic bacterium *Rhodobacter capsulatus* [see, Armstrong G. A., Alberti M., Leach F. and Hearst J. E. (1989) Nucleotide sequence, organization, and nature of the protein products of the carotenoid biosynthesis gene cluster of *Rhodobacter capsulatus*. Mol Gen Genet 216: 254–2681 and from the nonphotosynthetic bacteria *Erwinia herbicola* [see, Sandmann G., Woods W. S. and Tuveson R. W. (1990) Identification of carotenoids in *Erwinia herbicola* and in transformed *Escherichia coli* strain. FEMS Microbiol Lett 71: 77–82; Hundle B. S., Beyer P., Kleinig H., Englert H. and Hearst J. E. (1991) Carotenoids of *Erwinia herbicola* and an *Escherichia coli* HB101 strain carrying the *Erwinia herbicola* carotenoid gene cluster. Photochem Photobiol 54: 89–93; and, Schnurr G., Schmidt A. and Sandmann G. (1991) Mapping of a carotenogenic gene cluster from *Erwinia herbicola* and functional identification of six genes. FEMS Microbiol Lett 78: 157–162] and *Erwinia uredovora* [see, Misawa N., Nakagawa M., Kobayashi K., Yamano S., Izawa I., Nakamura K. and Harashima K. (1990) Elucidation of the *Erwinia uredovora* carotenoid biosynthetic pathway by functional analysis of gene products in *Escherichia coli*. J Bacteriol 172: 6704–6712]. Two genes, al-3 for GGPP synthase [see, Nelson M. A., Morelli G., Carattoli A., Romano N. and Macino G. (1989) Molecular cloning of a *Neurospora crassa* carotenoid biosynthetic gene (albino-3) regulated by blue light and the products of the white collar genes. Mol Cell Biol 9: 1271–1276; and, Carattoli A., Romano N., Ballario P, Morelli G. and Macino G. (1991) The *Neurospora crassa* carotenoid biosynthetic gene (albino 3). J Biol Chem 266: 5854–5859] and al-1 for phytoene desaturase [see, Schmidhauser T. J., Lauter F. R., Russo V. E. A. and Yanofsky C. (1990) Cloning sequencing and photoregulation of al-1, a carotenoid biosynthetic gene of *Neurospora crassa*. Mol Cell Biol 10: 5064–5070] have been cloned from the fungus *Neurospora crassa*. However, attempts at using these genes as heterologous molecular probes to clone the corresponding genes from cyanobacteria or plants were unsuccessful due to lack of sufficient sequence similarity.

The first "plant-type" genes for carotenoid synthesis enzyme were cloned from cyanobacteria using a molecular-genetics approach. In the first step towards cloning the gene for phytoene desaturase, a number of mutants that are resistant to the phytoene-desaturase-specific inhibitor, norflurazon, were isolated in Synechococcus sp. strain PCC 7942 [see, Linden H., Sandmann G., Chamovitz D., Hirschberg J. and Boger P. (1990) Biochemical characterization of Synechococcus mutants selected against the bleaching herbicide norflurazon. Pestic Biochem Physiol 36: 46–51]. The gene conferring norflurazon-resistance was then cloned by transforming the wild-type strain to herbicide resistance [see, Chamovitz D., Pecker I. and Hirschberg J. (1991) The molecular basis of resistance to the herbicide norflurazon. Plant Mol Biol 16: 967–974; Chamovitz D., Pecker I., Sandmann G., Boger P. and Hirschberg J. (1990) Cloning a gene for norflurazon resistance in cyanobacteria. Z Naturforsch 45c: 482–486]. Several lines of evidence indicated that the cloned gene, formerly called pds and now named crtP, codes for phytoene desaturase. The most definitive one was the functional expression of phytoene desaturase activity in transformed *Escherichia coli* cells [see, Linden H., Misawa N., Chamovitz D., Pecker I., Hirschberg J. and Sandmann G. (1991) Functional complementation in *Escherichia coli* of different phytoene desaturase genes and analysis of accumulated carotenes. Z Naturforsch 46c: 1045–1051; and, Pecker I. Chamovitz D., Linden H., Sandmann G. and Hirschberg J. (1992) A single polypeptide catalyzing the conversion of phytoene to ζ-carotene is transcriptionally regulated during tomato fruit ripening. Proc Natl Acad Sci USA 89: 4962–4966]. The crtP gene was also cloned from Synechocystis sp. strain PCC 6803 by similar methods [see, Martinez-Ferez I. M. and Vioque A. (1992) Nucleotide sequence of the phytoene desaturase gene from Synechocystis sp. PCC 6803 and characterization of a new mutation which confers resistance to the herbicide norflurazon. Plant Mol Biol 18: 981–983].

The cyanobacterial crtP gene was subsequently used as a molecular probe for cloning the homologous gene from an alga [see, Pecker I., Chamovitz D., Mann V., Sandmann G., Boger P. and Hirschberg J. (1993) Molecular characterization of carotenoid biosynthesis in plants: the phytoene desaturase gene in tomato. In: Murata N. (ed) Research in Photosynthesis, Vol III, pp 11–18. Kluwer, Dordrectht] and higher plants [see, Bartley G. E., Viitanen P. V., Pecker I., Chamovitz D., Hirschberg J. and Scolnik P. A. (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536; and, Pecker I., Chamovitz D., Linden H., Sandmann G. and Hirschberg J. (1992) A single polypeptide catalyzing the conversion of phytoene to ζ-carotene is transcriptionally regulated during tomato fruit ripening. Proc Natl Acad Sci USA 89: 4962–4966]. The phytoene desaturases in Synechococcus sp. strain PCC 7942 and Synechocystis sp. strain PCC 6803 consist of 474 and 467 amino acid residues, respectively, whose sequences are highly conserved (74% identities and 86% similarities). The calculated molecular mass is 51 kDa and, although it is slightly hydrophobic (hydropathy index −0.2), it does not include a hydrophobic region which is long enough to span a lipid bilayer membrane. The primary structure of the cyanobacterial phytoene desaturase is highly conserved with the enzyme from the green alga *Dunalliela bardawil* (61% identical and 81% similar; [see, Pecker I., Chamovitz D., Mann V., Sandmann G., Boger P. and Hirschberg J. (1993) Molecular characterization of carotenoid biosynthesis in plants: the phytoene desaturase gene in tomato. In: Murata N. (ed) Research in Photosynthesis, Vol III, pp 11–18. Kluwer, Dordrectht]) and from tomato [see, Pecker I., Chamovitz D., Linden H., Sandmann G. and Hirschberg J. (1992) A single polypeptide catalyzing the conversion of phytoene to ζ-carotene is transcriptionally regulated during tomato fruit ripening. Proc Natl Acad Sci USA 89: 4962–4966], pepper [see, Hugueney P., Romer S., Kuntz M. and Camara B. (1992) Characterization and molecular cloning of a flavoprotein catalyzing the synthesis of phytofluene and ζ-carotene in Capsicum chromoplasts. Eur J Biochem 209: 399–407] and soybean [see, Bartley G. E., Viitanen P. V., Pecker I., Chamovitz D., Hirschberg J. and Scolnik P. A. (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536] (62–65% identical and ~79% similar; [see, Chamovitz D. (1993) Molecular analysis of the early steps of carotenoid biosynthesis in cyanobacteria: Phytoene synthase and phytoene desaturase. Ph.D. Thesis, The Hebrew University of Jerusalem]). The eukaryotic phytoene desaturase polypeptides are larger (64 kDa); however, they are processed during import into the plastids to mature forms whose sizes are comparable to those of the cyanobacterial enzymes.

There is a high degree of structural similarity in carotenoid enzymes of *Rhodobacter capsulatus*, Erwinia sp. and *Neurospora crassa* [reviewed in Armstrong G. A., Hundle B. S. and Hearst J. E. (1993) Evolutionary conservation and structural similarities of carotenoid biosynthesis gene products from photosynthetic and nonphotosynthetic organisms. Meth Enzymol 214: 297–311], including in the crtI gene-product, phytoene desaturase. As indicated above, a high degree of conservation of the primary structure of phytoene desaturases also exists among oxygenic photosynthetic organisms. However, there is little sequence similarity, except for the FAD binding sequences at the amino termini, between the "plant-type" crtP gene products and the "bacterial-type" phytoene desaturases (crtI gene products; 19–23% identities and 42–47% similarities). It has been hypothesized that crtP and crtI are not derived from the same ancestral gene and that they originated independently through convergent evolution [see, Pecker I, Chamovitz D., Linden H., Sandmann G. and Hirschberg J. (1992) A single polypeptide catalyzing the conversion of phytoene to ζ-carotene is transcriptionally regulated during tomato fruit ripening. Proc Natl Acad Sci USA 89: 4962–4966]. This hypothesis is supported by the different dehydrogenation sequences that are catalyzed by the two types of enzymes and by their different sensitivities to inhibitors.

Although not as definite as in the case of phytoene desaturase, a similar distinction between cyanobacteria and plants on the one hand and other microorganisms is also seen in the structure of phytoene synthase. The crtB gene (formerly psy) encoding phytoene synthase was identified in the genome of Synechococcus sp. strain PCC 7942 adjacent to crtP and within the same operon [see, Bartley G. E., Viitanen P. V., Pecker I., Chamovitz D., Hirschberg J. and Scolnik P. A. (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536]. This gene encodes a 36-kDa polypeptide of 307 amino acids with a hydrophobic index of −0.4. The deduced amino acid sequence of the cyanobacterial phytoene synthase is highly conserved with the tomato phytoene synthase (57% identical and 70% similar; Ray J. A., Bird C. R., Maunders M., Grierson D. and Schuch W. (1987) Sequence of pTOM5, a ripening related cDNA from tomato. Nucl Acids Res 15: 10587–10588]) but is less highly conserved with the crtB sequences from other bacteria (29–32% identical and 48–50% similar with ten gaps in the alignment). Both types of enzymes contain two conserved sequence motifs also found in prenyl transferases from diverse organisms [see, Bartley G. E., Viitanen P. V., Pecker I., Chamovitz D., Hirschberg J. and Scolnik P. A. (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536; Carattoli A., Romano N., Ballario P, Morelli G. and Macino G. (1991) The *Neurospora crassa* carotenoid biosynthetic gene (albino 3). J Biol Chem 266: 5854–5859; Armstrong G. A., Hundle B. S. and Hearst J. E. (1993) Evolutionary conservation and structural similarities of carotenoid biosynthesis gene products from photosynthetic and nonphotosynthetic organisms. Meth Enzymol 214: 297–311; Math S. K., Hearst J. E. and Poulter C. D. (1992) The crtE gene in *Erwinia herbicola* encodes geranylgeranyl diphosphate synthase. Proc Natl Acad Sci USA 89: 6761–6764; and, Chamovitz D. (1993) Molecular analysis of the early steps of carotenoid biosynthesis in cyanobacteria: Phytoene synthase and phytoene desaturase. Ph.D. Thesis, The Hebrew University of Jerusalem]. It is conceivable that these regions in the polypeptide are involved in the binding and/or removal of the pyrophosphate during the condensation of two GGPP molecules.

The crtQ gene encoding ζ-carotene desaturase (formerly zds) was cloned from Anabaena sp. strain PCC 7120 by screening an expression library of cyanobacterial genomic DNA in cells of *Escherichia coli* carrying the Erwinia sp. crtB and crtE genes and the cyanobacterial crtp gene [see, Linden H., Vioque A. and Sandmann G. (1993) Isolation of a carotenoid biosynthesis gene coding for ζ-carotene desaturase from Anabaena PCC 7120 by heterologous complementation. FEMS Microbiol Lett 106: 99–104]. Since these *Escherichia coli* cells produce ζcarotene, brownish-red pigmented colonies that produced lycopene could be identified on the yellowish background of cells producing ζ-carotene. The predicted ζ-carotene desaturase from Anabaena sp. strain PCC 7120 is a 56-kDa polypeptide which consists of 499 amino acid residues. Surprisingly, its primary structure is not conserved with the "plant-type" (crP gene product) phytoene desaturases, but it has considerable sequence similarity to the bacterial-type enzyme (crtI gene product) [see, Sandmann G. (1993) Genes and enzymes involved in the desaturation reactions from phytoene to lycopene. (abstract), 10th International Symposium on Carotenoids, Trondheim CL1-2]. It is possible that the cyanobacterial crtQ gene and crtI gene of other microorganisms originated in evolution from a common ancestor.

The crtL gene for lycopene cyclase (formerly Lcy) was cloned from Synechococcus sp. strain PCC 7942 utilizing essentially the same cloning strategy as for crtP. By using an inhibitor of lycopene cyclase, 2-(4-methylphenoxy) triethylamine hydrochloride (MPTA), the gene was isolated by transformation of the wild-type to herbicide-resistance [see, Cunningham F. X. Jr, Chamovitz D., Misawa N., Gantt E. and Hirschberg J. (1993) Cloning and functional expression in *Escherichia coli* of a cyanobacterial gene for lycopene cyclase, the enzyme that catalyzes the biosynthesis of β-carotene. FEBS Lett 328: 130–138]. Lycopene cyclase is the product of a single gene product and catalyzes the double cyclization reaction of lycopene to β-carotene. The crtL gene product in Synechococcus sp. strain PCC 7942 is a 46-kDa polypeptide of 411 amino acid residues. It has no sequence similarity to the crtY gene product (lycopene cyclase) from *Erwinia uredovora* or *Erwinia herbicola*.

The gene for β-carotene hydroxylase (crtZ) and zeaxanthin glycosilase (crtX) have been cloned from *Erwinia herbicola* [see, Hundle B., Alberti M., Nievelstein V., Beyer P., Kleinig H., Armstrong G. A., Burke D. H. and Hearst J. E. (1994) Functional assignment of *Erwinia herbicola* Eho10 carotenoid genes expressed in *Escherichia coli*. Mol Gen Genet 254: 406–416; Hundle B. S., Obrien D. A., Alberti M., Beyer P. and Hearst J. E. (1992) Functional expression of zeaxanthin glucosyltransferase from *Erwinia herbicola* and a proposed diphosphate binding site. Proc Natl Acad Sci USA 89: 9321–9325] and from *Erwinia uredovora* [see, Misawa N., Nakagawa M., Kobayashi K., Yamano S., Izawa I., Nakamura K. and Harashima K. (1990) Elucidation of the *Erwinia uredovora* carotenoid biosynthetic pathway by functional analysis of gene products in *Escherichia coli*. J Bacteriol 172: 6704–6712].

The unicellular fresh-water green alga *Haematococcus pluvialis* accumulates large amounts of (3S,3'S) astaxanthin when exposed to unfavorable growth conditions, or following different environmental stresses such as phosphate or nitrogen starvation, high concentration of salt in the growth medium or high light intensity [see, Yong Y. Y. R. and Lee Y. K. (1991) Phycologia 30 257–261; Droop M. R. (1954) Arch Microbiol 20: 391–397; and, Andrewes A. G., Borch G., Liaaen-Jensen S. and Snatzke G. (1974) Acta Chem Scand B28: 730–736]. During this process, the vegetative cells of the alga form cysts and change their color from green to red. A cDNA from *Haematococcus pluvialis*, designated crtO, which encodes a β-C-4-oxygenase, the enzyme that converts β-carotene to canthaxanthin, and its expression in a heterologous systems expressing β-carotene hydroxylase (e.g., *Erwinia herbicola* crtZ gene product), leading to the production of (3S,3'S) astaxanthin are described in Harker M., Hirschberg J. (1997) Biosynthesis of ketocarotenoids in transgenic cyanobacteria expressing the algal gene for beta-C-4-oxygenase, crtO. FEBS Lett. 404:129–134.

The ketocarotenoid astaxanthin (3,3'-dihydroxy-β,β-carotene-4,4'-dione) was first described in aquatic crustaceans as an oxidized form of β-carotene. Astaxanthin was later found to be very common in many marine animals and algae. However, only few animals can synthesize astaxanthin de novo from other carotenoids and most of them obtain it in their food. In the plant kingdom, astaxanthin occurs mainly in some species of cyanobacteria, algae and lichens. However, it is found rarely also in petals of higher plant species [see, Goodwin T. W. (1980) The Biochemistry of the carotenoids, Vol. 1. 2nd Ed, Chapman and Hall, London and New York]. FIG. 2 presents the biosynthesis pathway of astaxanthin.

The function of astaxanthin as a powerful antioxidant in animals has been demonstrated [see, Miki W. (1991) Biological functions and activities of animal carotenoids. Pure Appl Chem 63: 141]. Astaxanthin is a strong inhibitor of lipid peroxidation and has been shown to play an active role in the protection of biological membranes from oxidative injury [see, Palozza P. and Krinsky N. I. (1992) Antioxidant effects of carotenoids in vivo and in vitro—an overview. Methods Enzymol 213: 403–420; and, Kurashige M., Okimasu E., Inove M. and Utsumi K. (1990) Inhibition of oxidative injury of biological membranes by astaxanthin. Physiol Chem Phys Med NMR 22: 27]. The chemopreventive effects of astaxanthin have also been investigated in which astaxanthin was shown to significantly reduce the incidence of induced urinary bladder cancer in mice [see, Tanaka T., Morishita Y., Suzui M., Kojima T., Okumura A. and Mori H. (1994). Chemoprevention of mouse urinary bladder carcinogenesis by the naturally occurring carotenoid astaxanthin. Carcinogenesis 15: 15]. It has also been demonstrated that astaxanthin exerts immunomodulating effects by enhancing antibody production [see, Jyonouchi H., Zhang L. and Tomita Y. (1993) Studies of immunomodulating actions of carotenoids. II. Astaxanthin enhances in vitro antibody production to T-dependent antigens without facilitating polyclonal B-cell activation. Nutr Cancer 19: 269; and, Jyonouchi H., Hill J. R., Yoshifumi T. and Good R. A. (1991) Studies of immunomodulating actions of carotenoids. I. Effects of β-carotene and astaxanthin on murine lymphocyte functions and cell surface marker expression in-vitro culture system. Nutr Cancer 16: 93]. The complete biomedical properties of astaxanthin remain to be elucidated, but initial results suggest that it could play an important role in cancer and tumor prevention, as well as eliciting a positive response from the immune system.

Astaxanthin is the principal carotenoid pigment of salmonids and shrimps and imparts attractive pigmentation in the eggs, flesh and skin [see, Torrisen O. J., Hardy R. W., Shearer K. D. (1989) Pigmentation of salmonid-carotenoid deposition and metabolism in salmonids. Crit Rev Aquatic Sci 1: 209]. The world-wide harvest of salmon in 1991 was approximately 720,000 MT., of which 25–30% were produced in a variety of aquaculture facilities [see, Meyers S. P. (1994) Developments in world aquaculture, feed formulations, and role of carotenoids. Pure Appl Chem 66: 1069]. This is set to increase up to 460,000 MT. by the year 2000 [see, Bjorndahl T. (1990) The Economics of Salmon Aquaculture. Blackwell Scientific, Oxford. pp. 1]. The red coloration of the salmonid flesh contributes to consumer appeal and therefore affects the price of the final product. Animals cannot synthesize carotenoids and they acquire the pigments through the food chain from the primary producers—marine algae and phytoplankton. Those grown in intensive culture usually suffer from suboptimal color. Consequently, carotenoid-containing nourishment is artificially added in aquaculture, at considerable cost to the producer.

Astaxanthin is the most expensive commercially used carotenoid compound (todays-1995 market value is of 2,500–3,500 $/kg). It is utilized mainly as nutritional supplement which provides pigmentation in a wide variety of aquatic animals. In the Far-East it is used also for feeding poultry to yield a typical pigmentation of chickens. It is also a desirable and effective nontoxic coloring for the food industry and is valuable in cosmetics. Recently it was reported that astaxanthin is a potent antioxidant in humans and thus is a desirable food additive.

Natural (3S,3'S) astaxanthin is limited in availability. It is commercially extracted from some crustacea species [see, Torrisen O. J., Hardy R. W., Shearer K. D. (1989) Pigmentation of salmonid-carotenoid deposition and metabolism in salmonids. Crit Rev Aquatic Sci 1: 209]. The (3R,3'R) stereoisomer of astaxanthin is produced from Phaffia [a yeast specie, see, Andrewes A. G., Phaff H. J. and Starr M. P. (1976) Carotenoids of *Phaffia rhodozyma*, a red-pigmented fermenting yeast. Phytochemistry Vol. 15, pp. 1003–1007]. Synthetic astaxanthin, comprising a 1:2:1 mixture of the (3S,3'S)-, (3S,3'R)- and (3R,3'R)-isomers is now manufactured by Hoffman-La Roche and sold at a high price (ca. $2,500/Kg) under the name "CAROPHYLL PINK" [see, Mayer H. (1994) Reflections on carotenoid synthesis. Pure & Appl Chem, Vol. 66, pp. 931–938]. Recently a novel gene involved in ketocompound biosynthesis, designated crtW was isolated from the marine bacteria *Agrobacterium auranticacum* and Alcaligenes PC-1 that produce ketocarotenoids such as astaxanthin. When the crtW gene was introduced into engineered *Eschrichia coli* that accumulated β-carotene due to Erwinia carotenogenic genes, the *Escherichia coli* transformants synthesized canthaxanthin a precursor in the synthetic pathway of astaxanthin [see, Misawa N., Kajiwara S., Kondo K., Yokoyama A., Satomi Y., Saito T., Miki W. and Ohtani T. (1995) Canthaxanthin biosynthesis by the conversion of methylene to keto groups in a hydrocarbon β-carotene by a single gene. Biochemical and biophysical research communications Vol. 209, pp. 867–876]. It is therefore desirable to find a relatively inexpensive source of (3S,3'S) astaxanthin to be used as a feed supplement in aquaculture and as a valuable chemical for various other industrial uses.

It is known that astaxanthin is contained in fishes such as red sea bream, salmon, trout, etc., and Crustacea such as shrimps, crabs, crawfishes and krills [Carotenoids of Marine Organisms; edt. Nippon Suisan Gakukai, 1978]. As microorganisms which produce astaxanthin, red yeast, *Phaffia rhodozyma* [Phytochemistry, 15, 1009, 1976], Brevibacterium [Journal of General and Applied Microbiology, 15, 127, 1969], and green algea *Haematococcus pluvialis* [Phytochemistry, 20, 2561, 1981] are known. As chemical Synthetic processes, conversion of β-carotene [Pure Appl. Chem. 57, 741, 1985] and synthesis from phosphonium salt [Helv. Chim. Acta. 64, 2436, 1981] are known.

However, the known process for production of astaxanthin are not advantageous due to high cost, because the content of astaxanthin in natural products such as krills, crawfishes, etc. is very low, and extraction thereof is difficult. In addition, stable availability of the resources is problematic. Moreover, slow growth rate and low astaxanthin productivity of the red yeast, *Phaffia rhodozyma*, makes this source of ketocarotenoids impractical from the industrial point of view.

The growth rate of the green algea, *Haematococcus pluvialis*, is also low, the culture is easily contaminated, and extraction of astaxanthin is extremely difficult because of the thick cell wall of this alga. Therefore, industrial production of astaxanthin from algea is difficult.

It is known that adonixanthin is contained in goldfishes and carps [Carotenoids of Marine Organisms, Nippon Suisan Gakukai, 1978], but it is believed that chemical synthesis of adonixanthin is difficult. No industrial process for production of adonixanthin is known.

As production processes for β-carotene, although synthesis from β-Ionone [Pure & Appl. Chem. 63(1), 45, 1991], and extraction from green or yellow vegetables such as carrot, sweet potato, pumpkin, etc., are known [Natural Coloring Agent Handbook, Korin, 1979, edt. by editorial committee of Natural Coloring Agent Handbook], production cost of these processes is high.

As processes for production of β-carotene by microorganisms, the production by an algea Dunaliella [J. Appl. Bacteriol., 70, 181, 1991], and the production by a fungus Blakeslea [J. Appl. Bacteriol., 70, 181, 1991] are known. Production of β-carotene by bacteria is also known for a certain bacterial species described in U.S. Pat. No. 5,607,839.

Echinenone is extracted from natural products, for example, starfishes such as crown-of-thorns starfish, the internal organs of fishes such as red sea bream, sea urchin, the internal organs of Crustacea such as lobster, etc. [Carotenoids of Marine Organisms, edt. Nippon Suisan Gakukai, 1987]. However, the production of echinenone by microorganisms is known only for a species of an unknown genus, described in U.S. Pat. No. 5,607,839.

Canthaxanthin is known to be contained in several species of mushrooms [Botanical Gazette, 112, 228–232, 1950], fishes, Crustacea etc. [Carotenoids of Marine Organisms, edt. Nippon Suisan Gakukai, 1978].

The production of echinenone by microorganisms are exemplified by the production by microorganisms belonging to the genus Brevibacterium [Applied and Environmental Microbiology, 55(10), 2505, 1989], and by microorganisms belonging to the genus Rhodococcus [Japanese Patent Publication No. 2-138996]. In addition, as chemical synthetic processes, oxidation of β-carotene [J. Amer. Chem. Soc., 78, 1427, 1956] and synthesis from novel compound 3-oxo-$C_{15}$ phosphonium salt [Pure & Appl. Chem. 51, 875, 1979] are known.

As processes for production of zeaxanthin, a chemical synthesis starting from a hydroxy ketone obtained by asymmetric reduction of oxoisophorone [Pure & Appl. Chem., 63(1), 45, 1991], extraction from corn seeds [Scitai Shikiso, 1974, Asakura Shoten], and a process using Flavobacterium [Carotenoids, In Microbial Technology, 2nd edn. Vol. 1, 529–544, New York: Academic Press] are known.

There is thus a widely recognized need for, and it would be highly advantageous to have, carotenoids, such as astaxanthin, producing and secreting bacteria, since such bacteria offer a readily available source of carotenoids.

Other features and advantages of the invention will become apparent from the following description and from the claims.

SUMMARY OF THE INVENTION

The present invention provides a novel bacterial species most similar to bacteria of the Paracoccus genus, as was determined by 16S ribosomal RNA analysis. The novel species produces and secretes carotenoid containing vesicles, which constitute another aspect of the present invention. Due to its 16S ribosomal RNA similarity to the Paracoccus genus the new species is referred to hereinbelow as *Paracoccus marcusii* strain MH1, however, it is most likely that the novel bacterium represents the first isolate of a new genus.

Eight distinct species are presently associated with the Paracoccus genus, although one of which presents a yellow pigment under some growth conditions, none of which produces carotenoids. Furthermore, no species belonging to the prokaryote kingdom is so far known to secrete substantial amounts of carotenoids to its growth medium during its life cycle (as opposed to decomposition processes). In addition, none of the bacterial species known to science secretes carotenoid containing vesicles to the growth medium.

Accordingly, the present invention further provides a process for production of carotenoids, such as, but not limited to, β-carotene, echinenone, β-cryptoxanthin, canthaxanthin, adonirubin, cis-adonixanthin, adonixanthin, astaxanthin and zeaxanthin, the process comprising culturing a bacterial species in a nutrient medium including sources of carbon, nitrogen and inorganic substances; and recovering an individual carotenoid pigment or a mixture of carotenoid pigments from the bacterial cells, vesicles secreted therefrom and/or the growth medium.

BRIEF DESCRIPTION OF THE DRAWINGS

The invention herein described, by way of example only, with reference to the accompanying drawings, wherein:

FIG. 3 shows some carotenoids produced by the novel species *Paracoccus marcusii* strain MH1;

DESCRIPTION OF THE PREFERRED EMBODIMENTS

Figure 1:
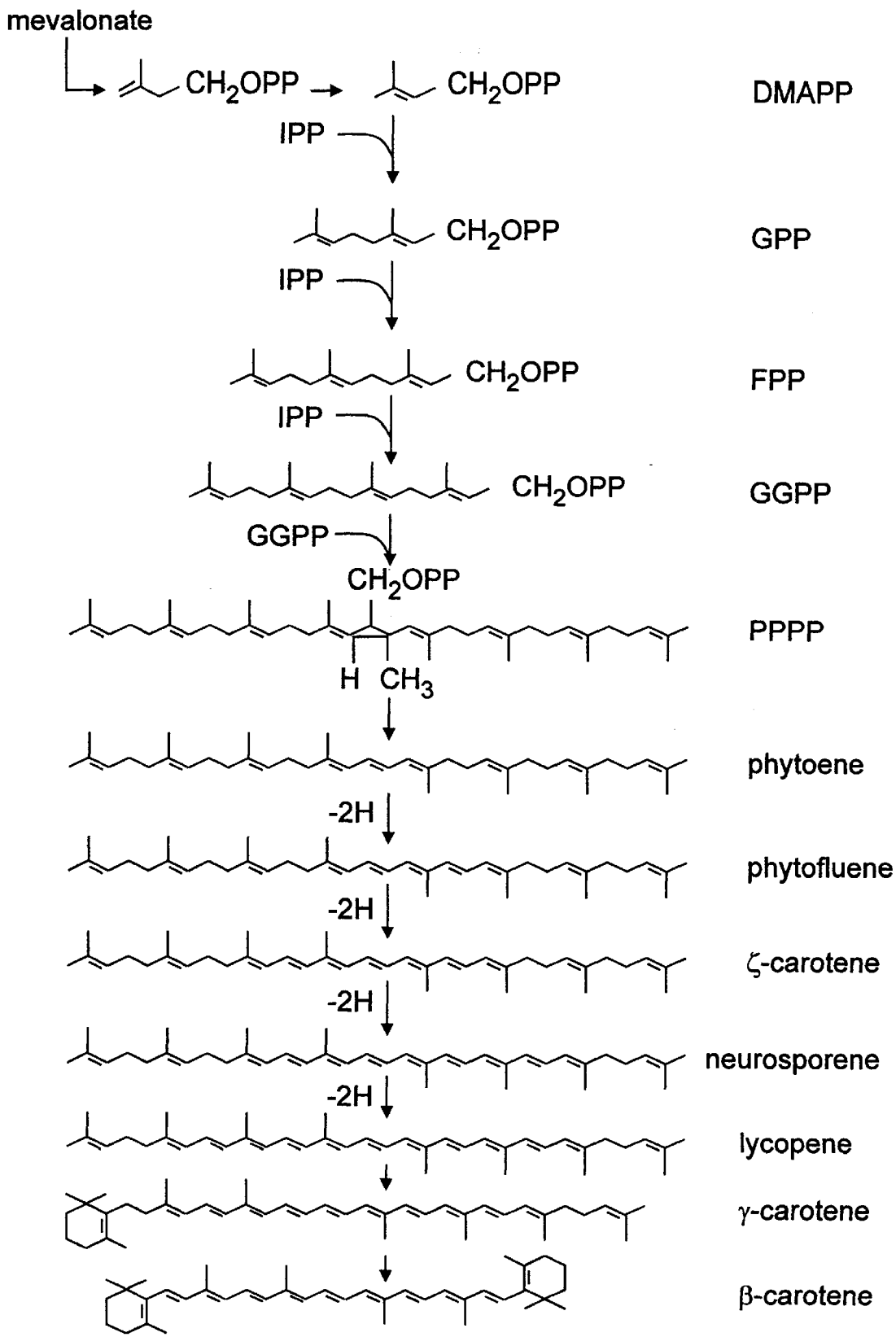
FIG. 1 shows the general biochemical pathway of β-carotene biosynthesis, in which pathway all molecules are depicted in an all-trans configuration, wherein IPP is isopentenyl pyrophosphate, DMAPP is dimethylallyl pyrophosphate, GPP is geranyl pyrophosphate, FPP is farnesyl pyrophosphate, GGPP is geranylgeranyl pyrophosphate and, PPPP is prephytoene pyrophosphate.
Figure 2:
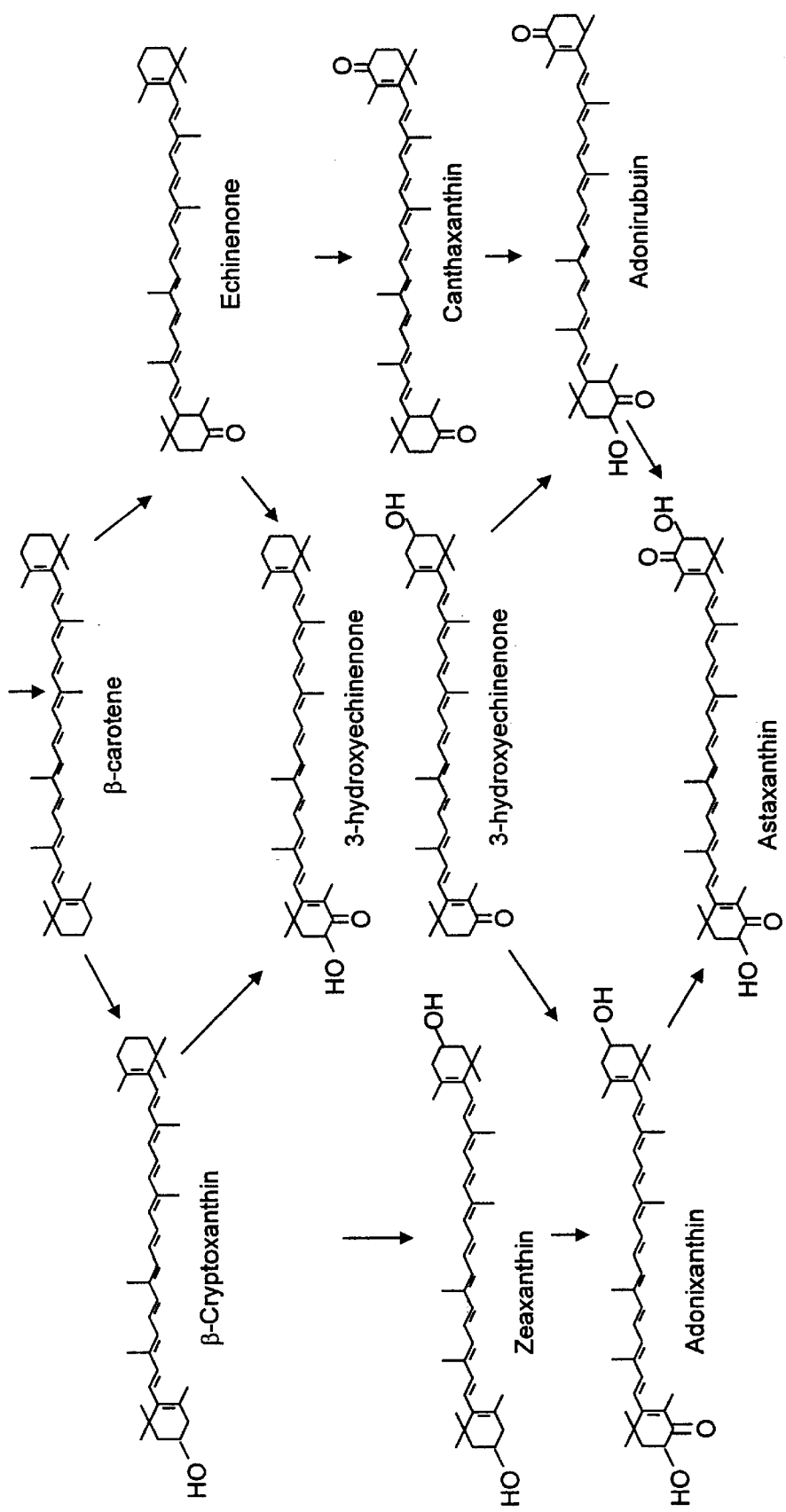
FIG. 2 shows the biosynthesis pathway of astaxanthin.

The present invention provides a novel bacterial species. Out of all the bacterial genera presently known, the novel bacterial species of the present invention is most similar to the genus Paracoccus, as determined by 16S ribosomal RNA homology analysis. However, the novel species produces and secretes carotenoid vesicles, a yet unreported phenomenon, and is therefore considered the first isolate of a new genus. The present invention further provides a process for production of carotenoids using a bacterial species secreting same to the growth medium and few products and preparations thus obtainable.

The term "vesicle" as used herein in the specification and claims below refers to any substantially globular lipophillic body which is not a life form, i.e., is not capable of reproduction. Such use of the term is acceptable in the art of biology.

It should be noted that prokaryotes taxonomy is often subjected to changes due to new findings and/or new evaluation of existing findings. Accordingly, since the novel bacterial species of the present invention produces carotenoids, whereas all other known members of the genus Paracoccus do not, it is, therefore, postulated that the novel bacterial species is a member of a novel, yet unknown, genus. The fact that the novel species also secretes carotenoids in a vesicular form, distinguishes the novel species from all other prokaryotes and strengthens the notion that it is the first representative of a new genus.

The term "most similar" as used in the specification and claims, refers only to prior art bacterial genera, wherein similarity is based on 16S ribosomal RNA homology analysis. In one aspect, the invention therefore relates to any carotenoid producing bacterial species which is most similar, as far as 16S ribosomal RNA is concerned, to species of the genus Paracoccus. In another aspect the present invention relates to any carotenoid producing and secreting bacterial species.

The genus Paracoccus consists of gram-negative cocci or short rods, showing a substantial metabolic versatility. Representatives are able to grow aerobically on a wide range of organic compounds. A number of species can grow anaerobically as well, using nitrate as electron acceptor, and some representatives are able to use hydrogen as electron donor for chemoautotrophic growth. Phylogenetically the genus belongs to the α-3 subclass of the Proteobacteria.

Presently eight species are recognized within the genus Paracoccus: *P. denitrificans* (the type species of the genus) [van Verseveld, H. W., and A. H. Stouthamer. 1992. The genus Paracoccus, p. 2321–2334. In A. Balows, H. G. Trüper, M. Dworkin, and K.-H. Schleifer (ed.), prokaryotes. A handbook on the biology of bacteria: ecophysiology, isolation, identification, applications, 2nd. ed., vol. 3. Springer-Verlag, New York; and Visuvanathan, S., M. T. Moss, J. L. Stanford, J. Hermon-Taylor, and J. J. McFadden. 1989. Simple enzymatic method for isolation of DNA from diverse bacteria. J. Microbiol. Meth. 10:59–64], *P. thiocyanatus* [Katayama, Y., A. Hiraishi, and H. Kuraishi. 1995. *Paracoccus thiocyanatus* sp. nov., a novel species of thiocyanate-utilizing facultative chemolithotroph, and transfer of *Thiobacillus versutus* to the genus Paracoccus as *Paracoccus versutus* comb. nov. with emendation of the genus. Microbiology 141:1469–1477], P. versutus (formerly known as *Thiobacillus versulus*) [Katayama, Y., A. Hiraishi, and H. Kuraishi. 1995. *Paracoccus thiocyanatus* sp. nov., a new species of thiocyanate-utilizing facultative chemolithotroph, and transfer of *Thiobacillus versutus* to the genus Paracoccus as *Paracoccus versutus* comb. nov. with emendation of the genus. Microbiology 141:1469–1477], *P. kocurii* [Ohara, M., Y. Katayama, M. Tsuzaki, S. Nakamoto, and H. Kuraishi. 1990. *Paracoccus kocurii* sp. nov., a tetramethylammonium-assimilating bacterium. Int. J. Syst. Bacteriol. 40:292–296], *P. alcaliphilus* [Urakami, T., J. Tamaoka, K. Suzuki, and K. Komagata. 1989. *Paracoccus alcaliphilus* sp. nov., an alkaliphilic and facultatively methylotrophic bacterium. Int. J. Syst. Bacteriol. 39:116–121], *P. aminophilus, P. aminovorans* [Urakami, T., H. Araki, H. Oyanagi, K. Suzuki, and K. Komagata. 1990. *Paracoccus aminophilus* sp. nov. and *Paracoccus aminovorans* sp. nov., which utilize N,N'-dimethylformamide. Int. J. Syst. Bacteriol. 40:287–291], and *P. solventivorans* [Siller, H., F. A. Rainey, E. Stackebrandt, and J. Winter. 1996. Isolation and characterization of a new gram-negative, acetone degrading, nitrate-reducing bacterium from soil, *Paracoccus solventivorans* sp. nov. Int. J. Syst. Bacteriol. 46:1125–1130].

The strain previously known as *P. halodenitrificans* has recently been transferred to the genus Halomonas on account of its phylogenetic affiliation [Dobson, S. J., and P. D. Franzmann. 1996. Unification of the genera Deleya (Baumann et al. 1983), Halomonas (Vreeland et al. 1980), and Halovibrio (Fendrich 1988) and the species *Paracoccus denitrificans* (Robinson and Gibbons 1952) into a single genus, Halomonas, and placement of the genus Zymnobacter in the family Halomonadaceae. Int. J. Syst. Bacteriol. 46:550–558].

None of the eight known members of the Paracoccus genus produces carotenoids.

A gram-negative brightly orange coccoid bacterium that appeared as a contaminant on a nutrient agar plate was isolated and characterized as further detailed below.

Phenotypic characterization and phylogenetic analysis based on 16S rDNA sequence comparisons showed that the bacterium should be classified as a hitherto unknown species within the genus Paracoccus. Here we propose the name *Paracoccus marcusii* sp. nov. for this isolate, and describe its characteristics.

Yet, as already stated above, and as is further demonstrated in the Examples section below, the novel bacterial species both produces and secretes carotenoids in dedicated vesicles, a phenomenon yet unreported for any prokaryote. As such, the novel bacterial species of the present invention most likely represents the first isolate of a new genus.

Important features of the new isolate are both the production and the vesicular secretion to the medium of a variety of carotenoids, whereas non of the bacterial species so far known both produces and secretes carotenoids during their life cycle. Therefore, according to another aspect, the present invention relates to any bacterial species which secretes carotenoids during its life cycle (as opposed to decomposition associated secretion), in particular strains which secrete carotenoid vesicles.

Since caratenoids secrition is vesicular, another aspect of the invention concerns carotenoid containing vesicles, preparation and medium containing same.

The new isolate produces and secretes β-carotene, echinenone, β-cryptoxanthin, canthaxanthin, adonirubin, cis-adonixanthin, adonixanthin, astaxanthin and zeaxanthin. Thus, another aspect of the invention concerns caratenoids produced according to any of the processes for carotenoid production according to the invention as described herein.

Accordingly, another aspect of the present invention relates to a process for production of at least one carotenoid pigment such as, but not limited to, β-carotene, echinenone, β-cryptoxanthin, canthaxanthin, adonirubin, cis-adonixanthin, adonixanthin, astaxanthin and zeaxanthin. Some of these carotenoids are represented by their formulations in FIG. 3.

The process includes the following steps. First a bacterial species most similar to the Paracoccus genus is cultured in an aqueous or solid nutrient medium including sources of carbon, nitrogen and inorganic substances to support its growth, production of carotenoid pigments and preferably their secretion to the growth medium. Second, an individual carotenoid pigment or a mixture of carotenoid pigments are recovered either from the medium and/or the cells of the species. One ordinarily skilled in the art would know how to design the exact growth and recovering procedures to maximize yields.

According to the present invention any bacterial species which secretes carotenoids or any species which produces carotenoids and is most similar to the genus Paracoccus, as the term "most similar" is used herein can be used.

Among those bacteria, as a particular microorganism *P. marcusii* MH1 strain can be mentioned. This strain was newly isolated by the present inventors, and has been deposited under the Budapest Treaty in the Deutsche Sammlung von Mikroorganismen und Zellkulturen, on Jun. 4, 1997, as strain DSM 11574$^T$.

Nucleotide sequence of DNA coding for 16S ribosomal RNA of the *P. marcusii* MH1 strain is shown in SEQ ID NO: 1.

Medium for production of carotenoids using the present microorganisms is, for example, as follows. Namely, it contains a carbon source, a nitrogen source and inorganic salts necessary for the growth of producer microorganisms, as well as if necessary special required substances (for example, vitamins, amino acids, nucleic acids etc.).

As the carbon sources, sugars such as glucose, sucrose, lactose, fructose, trehalose, mannose, mannitol, maltose, etc.; organic acids such as acetic acid, fumaric acid, citric acid, propionic acid, malic acid, pyruvic acid, malonic acid; alcohols such as ethanol, propanol, butanol, pentanol, hexanol, isobutanol, glycerol; oil or fat such as soybean oil, rice bran oil, olive oil, corn oil, sesame oil, linseed oil, and the like are mentioned. Amount of the carbon source added varies according to the kind of the carbon source, and usually 1 to 100 g, preferably 2 to 50 g per 1 liter medium.

As the nitrogen sources, for example, potassium nitrate, ammonium nitrate, ammonium chloride, ammonium sulfate, ammonium phosphate, ammonia, urea etc., are used alone or in combination. Amount of the nitrogen source added varies according to the kind of the nitrogen source, and usually 0.1 to 30 g, and preferably 1 to 10 g per 1 liter medium.

As the inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc, chloride, cupric sulfate, calcium chloride, calcium carbonate, sodium carbonate, etc., may be used alone or in combination. Amount of inorganic acid varies according to the kind of the inorganic salt, and usually 0.001 to 10 g per 1 liter medium.

As special required substances, vitamins, nucleic acids, yeast extract, peptone, meat extract, malt extract, corn steep liquor, soybean meal, dried yeast etc., may be used alone or in combination. Amount of the special required substance used varies according to the kind of the substance, and usually ranges between 0.2 g to 200 g, and preferably 3 to 100 g per 1 liter medium.

A pH value 5 of a medium is adjusted to pH 2 to 12, preferably 6 to 9. Culturing is carried out at temperature of 15 to 40° C., and preferably 20 to 35° C., usually for 1 to 20 days, and preferably 1 to 4 days, under aerobic condition provided by shaking or aeration/agitation.

Finally the carotenoid(s) may be isolated and purified from the culture. Namely, microbial cells are separated from the culture by a conventional means such as centrifugation or filtration, and the cells or the medium are subjected to an extraction with a suitable solvent. As an optional prefered step prior to extraction carotenoid loaded vesicles may be recovered from the medium, by for example, ultracentrifugation or filtration.

As a solvent for the extraction, any substance in which the carotenoids are soluble can be used. For example, organic solvents such as acetone, chloroform, dichloromethane, hexane, cyclohexane, methanol, ethanol, isopropanol, benzene, carbon disulfide, diethyl ether etc., are used, and preferably chloroform, dichloromethane, acetone, methanol, ethanol or isopropanol is used. The purification can be carried out by conventional procedures such as absorption, elution, dissolving and the like, alone or preferably in combination.

According to the present invention, in many cases, β-carotene, echinenone, β-cryptoxanthin, canthaxanthin, adonirubin, cis-adonixanthin, adonixanthin, astaxanthin and zeaxanthin are simultaneously produced and present in the cultured cells and/or medium.

Accordingly, in an embodiment of the present invention, any one of the above-mentioned carotenoids or others can be singly obtained by the above-mentioned procedure. Alternatively, a mixture of the carotenoids also can be obtained. In this way, the process for carotenoid production of the present invention includes a process for production of an individual carotenoid and a process for production of a mixture of the carotenoids.

Astaxanthin and adonixanthin can be separated from each other according to a conventional procedure for mutual separation of carotenoids, such as adsorption/elution column chromatography, differential extraction, counter current extraction and differential crystallization. In addition, for production of an individual carotenoid, the desired carotenoid may be preferentially produced by controlling medium composition, culture conditions and the like.

For example, a ratio of carotenoids produced can be changed by changing an aerobic condition. For example, a ratio of carotenoids produced may be changed by an amount of a medium or a rate of shaking in flask-shaking culture, or by changing a rate of air supply or a rate of agitation in an aeration/agitation culture.

Alternatively, for preferential production of a particular carotenoid, a producer microorganism can be improved by a mutation such as artificial mutation of the producer microorganism so that a mutant microorganism preferentially produces the desired carotenoid among others. Such mutation treatments include, for example, physical methods such as X-ray radiation, UV radiation and the like; chemical methods such as the use of N-methyl-N'-nitro-N-nitrosoguanidine (NTG), ethylmethane sulfonate (EMS); and a biological methods such as gene recombination technique.

Processes for production of the carotenoids using such an improved mutant are included in the present process for production of carotenoids.

In astaxanthin produced by the present process as described above, purity of (3S,3'S)-astaxanthin is almost 100%. It is known that a ratio of (3S,3'S)-astaxanthin in astaxanthin contained in natural products such as crawfish, Haematococcus, salmon, trout, red sea bream is high. On the other hand, it is known that *Phaffia rhodozyma* contains (3R,3'R)-astaxanthin in a high ratio, which absolute configuration is the opposite of that of astaxanthin contained in most of natural products.

Almost 100% of astaxanthin produced by the present process is (3S,3'S)-astaxanthin whose absolute configuration is same as that of a majority of naturally occurring astaxanthin, and therefore astaxanthin produced by the present process is industrially valuable. In addition, although chemical synthesis of (3S,3'S)-astaxanthin is known (Helv. Chim. Acta, 61, 2609, 1978), since optically pure (4R, 6R)-4-hydroxy-2,2,6-trimethylcyclohexanone is used as a starting material, the process is of high cost, and industrially not advantageous.

In addition, astaxanthin produced by the present process contains substantially all-trans astaxanthin. The all-trans astaxanthin is of natural form, and the present producer microorganisms are advantageous in that they produce natural type astaxanthin. Where cis-astaxanthin is necessary, this can be obtained from all-trans astaxanthin according to a known process, while it is difficult to prepare all-trans astaxanthin from cis-astaxanthin.

Reference in now made to the following examples, which together with the above descriptions, illustrate the invention.

EXAMPLES

The following protocols and experimental details are referenced in the Examples that follow:

Source of organism. The strain, designated further on as Paracoccus strain MH1 or *Paracoccus marcusii* sp. nov., appeared as a single brightly orange colony contaminating a nutrient agar plate.

Media and culture conditions. Paracoccus strain MH1 was routinely grown at 25° C. in medium containing (per liter): 10 g of Bacto-tryptone, 5 g of Bacto-yeast extract, and 5 g of NaCl, pH 7.0. Liquid cultures were grown on a shaking water bath. For solid media 15 g of Bacto-agar was added per liter. The composition of this medium was modified by the addition of $NaNO_3$, starch, increased NaCl concentrations, and other components, as specified in the following Examples.

Microscopy. Cultures were examined and photographed using a Zeiss Standard microscope, equipped with phase contrast optics.

Physiological and biochemical characterization. Tests for properties such as the presence of catalase, cytochrome oxidase, urease, arginine dehydrolase, amylase, and anaerobic growth on nitrate were performed using standard methods as described in Holding, A. J., and J. G. Collee. 1971. Routine biochemical tests, p. 1–32. In J. R. Norris, and D. W. Ribbons (ed.), Methods in microbiology, vol. 6A. Academic Press, London.

Selected physiological traits were determined with the API 20 NE system (BioMérieux, Marcy-l'Etoile, France), which examines nine metabolic capacities (reduction of nitrate, formation of indole from tryptophan, acid formation from glucose, arginine dihydrolase, urease, hydrolysis of gelatin and esculin, and β-galactosidase) and aerobic growth on 12 carbon sources (glucose, arabinose, mannose, mannitol, N-acetylglucosamine, maltose, gluconate, caprate, adipate, malate, citrate and phenylacetate). All API tests were performed in accordance with the manufacturer's directions.

To test utilization of additional carbon sources, Biolog Inc. (Hayward, Calif.) SF-N MicroPlate microtiter plates with 95 substrates were used. Cells were suspended in the AUX medium of the API 20 NE system (containing per liter: 2 g of $(NH_4)_2SO_4$, 1.5 g of agar, 82.8 mg of mineral base, 250 mg of amino acids, 45.9 mg of vitamins/nutritional substances, and 40 mM of phosphate buffer pH 7.0). Portions of 140 μl were added to the wells of the Biolog microtiter plates, and after 2–3 days of incubation at 30° C. the wells were examined for growth.

Growth on selected substrates was further tested in 100 ml Erlenmeyer flasks with 30 ml portions of liquid medium containing (per liter): 0.5 g of Bacto-tryptone, 0.25 g of Bacto-yeast extract, 5 g of NaCl, and 5 mM of HEPES, pH 7.0. This low nutrient medium was amended with 2.5 g per liter of the substance to be tested, and growth was compared with that in non-amended medium.

Fatty acid analysis was performed essentially as described in Siller H., Rainey F. A., Stackberandt E. and Winter J. (1996) Isolation and characterization of a new Gram-negative acetone-degrading, nitrate-reducing bacterium from soil, Paracoccus solventivorans sp. nov. J. Sys. Bacteriol. 46:1125–1130. Formation of poly-β-hydroxyalkanoate was tested by extracting dry cell pellets with chloroform, drying the extract, and assessing the formation of crotonate spectrophotometrically after heating with concentrated sulfuric acid.

DNA base composition. The DNA was isolated and purified by chromatography on hydroxyapatite according to Visuvanathan et al. [Visuvanathan, S., M. T. Moss, J. L. Stanford, J. Hermon-Taylor, and J. J. McFadden. 1989. Simple enzymatic method for isolation of DNA from diverse bacteria. J. Microbiol. Meth. 10:59–64]. The G+C content was determined by using high-performance liquid chromatography (HPLC) as described by Mesbah et al. [Mesbah, M., U. Premachandran, and W. B. Whitman. 1989. Precise measurement of the G+C content of deoxyribonucleic acid by high performance liquid chromatography. Int. J. Syst. Bacteriol. 39:159–167].

Sequencing of the 16S rDNA gene. Genomic DNA extraction, PCR-mediated amplification of the 16S rDNA and purification of the PCR products was carried out as described [De Soete, G. 1983. A least square algorithm for fitting additive trees to proximity data. Psychometrika 48:621–626]. Purified PCR products were sequenced using the ABI PRISM™ Dye Terminator Sequencing Ready Reaction Kit (Applied Biosystems, Germany) as directed in the manufacturer's protocol. Sequence reactions were electrophoresed using the Applied Biosystems 373A DNA Sequencer. The resulting sequence data were put into the alignment editor ae2 [Maidak, B. L., G. J. Olsen, N. Larsen, M. J. McCaughey, and C. R. Woese. 1996. The Ribosomal Database Project (RDP). Nucleic Acids Res. 24:82–85], aligned manually, and compared with representative 16S rRNA gene sequences belonging to the Rhodobacter group of the α-subdivision of the Proteobacteria. For comparison, 16S rRNA sequences were obtained from the EMBL data base of the Ribosomal Database Project [Maidak B. L., G. J. Olsen, N. Larsen, M. J. McCaughey, and C. R. Woese. 1996. The Ribosomal Database Project (RDP). Nucleic Acids Res. 24:82–85]. For construction of the phylogenetic dendrogram operations of the PHYLIP package [Felsenstein, J. 1993. PHYLIP (Phylogeny Inference Package), version 3.5.1. Department of Genetics, University of Washington, Seattle] were used. Pairwise evolutionary distances were computed from percent similarities by the correction of Jukes and Cantor [Jukes, T. H., and C. R. Cantor. 1969. Evolution of protein molecules, p. 21–132. In H. N. Munro (ed.), Mammalian protein metabolism. Academic Press, New York]. A phylogenetic tree was constructed by the neighbor-joining method based on the evolutionary distance values [Saitou, N. and M. Nei. 1987. The neighbor-joining method: a new method for reconstructing phylogenetic trees. Mol. Biol. Evol. 4:406–425]. The least-squares distance method of De Soete [De Soete, G. 1983. A least square algorithm for fitting additive trees to proximity data. Psychometrika 48:621–626] was used in the construction of the phylogenetic dendrogram. The root of the tree was determined by including the 16S rRNA gene sequence of *Roseobacter denitrificans* ATCC 33942$^T$ into the analysis.

Nucleotide sequence accession number. The 16S rDNA gene sequence of *Paracoccus marcusii* DSM 11574$^T$ has been assigned EMBL Nucleotide Sequence Data Base accession number Y12703.

Carotenoids analysis. Aliquots of *P. marcusii* cells were harvested by centrifugation at 13,000×g for 10 min and washed once in water. Aliquots of vesicles of secreted by *P. marcusii* were harvested by ultracentrifugation at 40,000 rpm in an ultracentrifuge (Beckman L8, rotor SW50.1, 192,000 g). The cells, vesicles were resuspended in 200 μl acetone and incubated at 65° C. for 10 min in the dark. For cells depleted medium extraction, 10 μl of medium were mixed with 200 μl acetone and incubated at 65° C. for 10 min in the dark. The samples were centrifuged again at 13,000×g for 10 min and the acetone supernatant containing the pigments was placed in a clean tube. The pigment extract was blown to dryness under a stream of $N_2$ and stored at −20° C. until required for analysis.

Reversed phase HPLC was carried out using a Spherisorb ODS2, 5 μm column (25.0 cm×0.46 cm) with a 2 cm guard column. A solvent gradient of 0–60% A (0–10 min), 60–76% A (10–15 min), 76% A (15–22 min), 76–100% A (22.1–28.0 min), at a flow rate of 1 ml per minute (A=ethyl acetate, B=acetonitrile/water (9/1 v/v)) was used. Solvents were pumped using a CM4000 triphasic pump system. The samples were injected in 20 μl aliquots via an on-line Rheodyne injector unit. A HP1040A diode-array detector was used to monitor spectra on line and to integrate chromatograms.

TLC was carried out on Kieselgel 60 $F_{254}$ silica plates. $R_F$ values refer to solvent systems of diethyl ether (TLC system 1) and hexane/ethyl acetate (3/2 v/v) (TLC system 2) respectively.

UV/Visible electronic absorption spectra were recorded in redistilled or HPLC grade acetone and diethyl ether. The spectra were recorded using a Cecil CE 5501 computing double beam UV/Visible spectrophotometer. The degree of fine structure is expressed as the ratio of the peak heights of %III/II where the zero value is taken as the minimum between the two absorption peaks, the peak height of the longest wavelength absorption wavelength is designated III, and that of the middle absorption wavelength as II. In the case of conjugated ketocarotenoids, such as astaxanthin, which exhibits a single absorption peak with no fine structure, the %III value is zero.

Mass spectrometry was carried out using positive-ion EI on a VG 7070H double focusing magnetic sector mass spectrometer, operating at a low resolution (ca. 1000). Data acquisition and processing was by a Finnigan INCOS 2300 data system. Full scan MS were recorded over the m/z range 40–700 at an accelerating voltage of 2 kV in a total cycle time of 3.5 sec. The probe temperature was raised gradually from ambient to above 300° C. in ca. 5 min. The spectra were recorded at an ionisation potential of 70 eV.

Electron microscopy. Samples for electron microscopy were fixed overnight in 3% glutaraldehyde in 0.1 M cacodylate buffer pH 7.4, washed in the same buffer and post-fixed with 1% $OsO_4$ in 0.1 M cacodylate buffer for 2 hours. Dehydration was done in a series of ethyl alcohol and propylene oxide concentrations and embedded in Epon-812. The ultra-thin sections were stained with uranyl acetate and lead citrate prior to viewing in a Jeol-1000 CX electron microscope.

Chirality configuration. Chirality configuration of astaxanthin was determined by HPLC of the derived diastereoisomeric camphanates of the astaxanthin [Renstrom B., Borch G., Skulberg M. and Liaaen-Jensen S (1981) Optical purity of (3S,3S')-astaxanthin from *Haematococcus pluvialis*. Phytochem 20: 2561–2565].

Example 1

Morphological features of Paracoccus MH1

Figure 4:
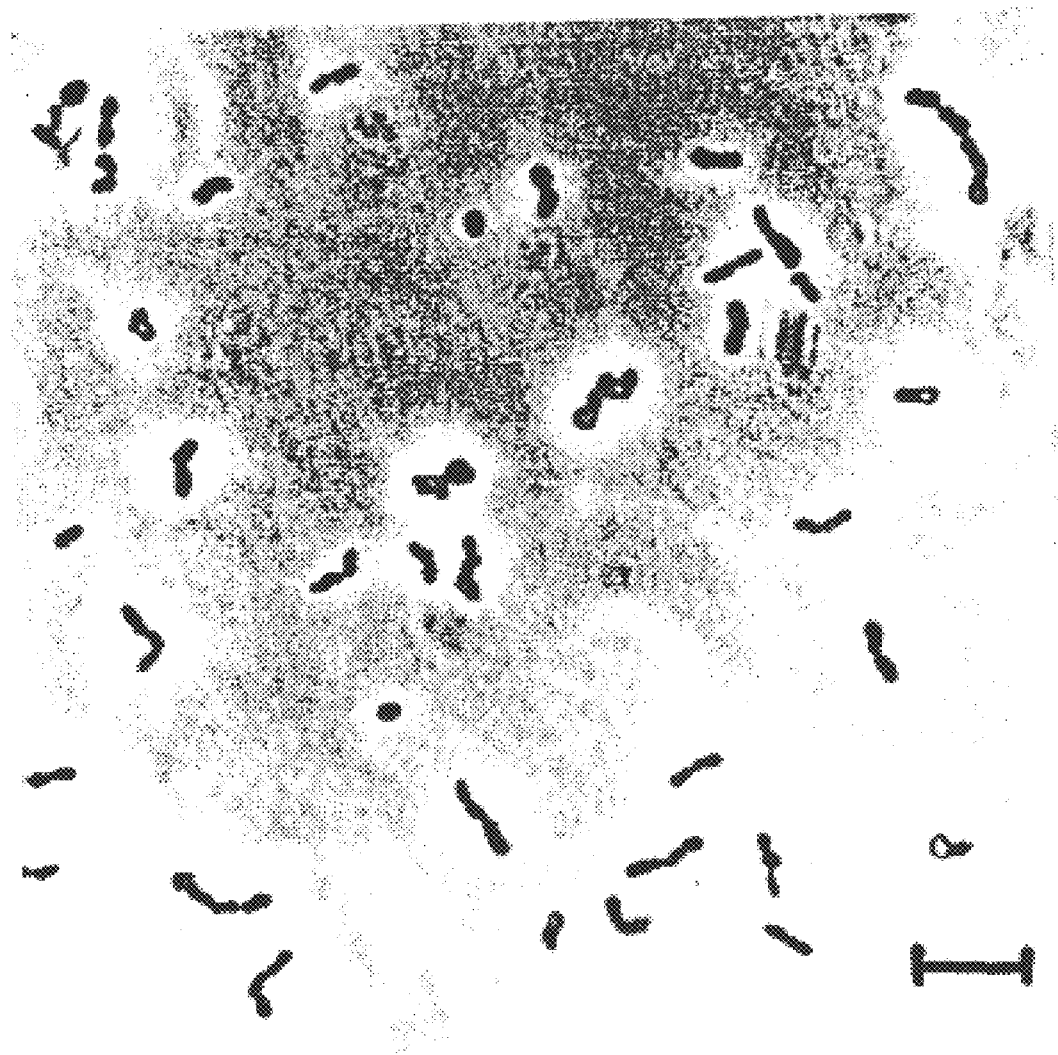
FIG. 4 shows a phase-contrast micrograph of *Paracoccus marcusii* strain MH1, wherein the bar equals 10 μm.

As shown in FIG. 4, *Paracoccus marcusii* strain MH1 formed cocci to short rods, 1 to 2 by 1 to 1.5 μm in size. It consisted mainly of pairs and short chains or clusters of up to 4–5 bacteria. Cells were nonmotile, and did not form spores. Strain MH1 stained gram-negative. Colonies on agar were smooth, flat, brightly orange colored.

Example 2

Physiological and biochemical characterization

Optimum temperature for growth was 25–30° C. At 35° C. growth was poor. Doubling time in the standard growth medium at the optimal temperature was 2.3 h. When the NaCl concentration in the medium was increased to 6 g per liter, growth was slow, and above 8 g per liter of NaCl no growth was obtained.

The following carbon and energy sources could be used for growth: D-glucose, D-fructose, D-galactose, D-mannose, L-arabinose, maltose, cellobiose, D-lactose, melibiose, sucrose, turanose, D-trehalose, gentobiose, lactulose, D-gluconic acid, D-glucuronic acid, D-galacturonic acid, glycerol, erythritol, D-mannitol, D-sorbitol, xylitol, m-inositol, adonitol, D-arabitol, propionic acid, cis-aconitic acid, citric acid, DL-lactic acid, malonic acid, quinic acid, succinic acid, malic acid, formic acid, L-alanine, and alaninamide. Esculin and p-nitrophenyl-β-D-galactopyranoside were hydrolyzed (β-glucosidase and β-galactosidase activity). No growth was obtained on L-fucose, D-psicose, L-rhamnose, raffinose, dextrin, glycogen, N-acetyl-D-glucosamine, N-acetyl-D-galactosamine, β-methyl-D-glucoside, DL-α-glycerolphosphate, glucose-1-phosphate, glucose-6-phosphate, methanol, 2,3-butanediol, methylamine.HCl, trimethylamine.HCl, dimethylformamide, $Na_2S_2O_3$, Tween 40, Tween 80, acetic acid, α-hydroxybutyric acid, β-hydroxybutyric acid, γ-hydroxybutyric acid, α-ketobutyric acid, α-ketovaleric acid, capric acid, adipic acid, phenylacetic acid, methylpyruvic acid, glycine, D-alanine, L-alanylglycine, L-asparagine, L-aspartate, L-glutamate, L-histidine, L-leucine, L-ornithine, L-phenylalanine, L-proline, L-serine, D-serine, L-threonine, DL-carnithine, γ-aminobutyric acid, inosine, uridine, and thymidine. Starch was not hydrolyzed. Gelatin hydrolysis was weak or absent. Arginine dihydrolase and urease activities were not detected. No indole was produced from tryptophan.

Metabolism is obligatory aerobic. Cytochrome oxidase and catalase reactions were positive. Nitrate did not support anaerobic growth, and was not reduced to nitrite. Glucose was not fermented.

The fatty acid profile (79.4% of C18:1, 5.0% of C18:0, 6.2% of C10:0, and 9.4% in two unknown peaks) is characteristic of the α-subgroup of the Proteobacteria. Poly-β-hydroxyalkanoate was not detected.

A very pronounced feature of Paracoccus strain MH1 is its intense orange pigmentation. With the exception of *P. thiocyanalus*, which has been described as forming reddish-yellow colonies on certain growth media [Katayama, Y., A. Hiraishi, and H. Kuraishi. 1995. *Paracoccus thiocyanatus* sp. nov., a new species of thiocyanate-utilizing facultative chemolithotroph, and transfer of *Thiobacillus versutus* to the genus Paracoccus as *Paracoccus versutus* comb. nov. with emendation of the genus. Microbiology 141:1469–1477], all other Paracoccus species are colorless.

Example 3

G+C content of DNA

The G+C content of the DNA of strain MH1 was 66 mol % as was determined by HPLC analysis.

Example 4

Phylogenetic relationships of strain MH1

Figure 5:
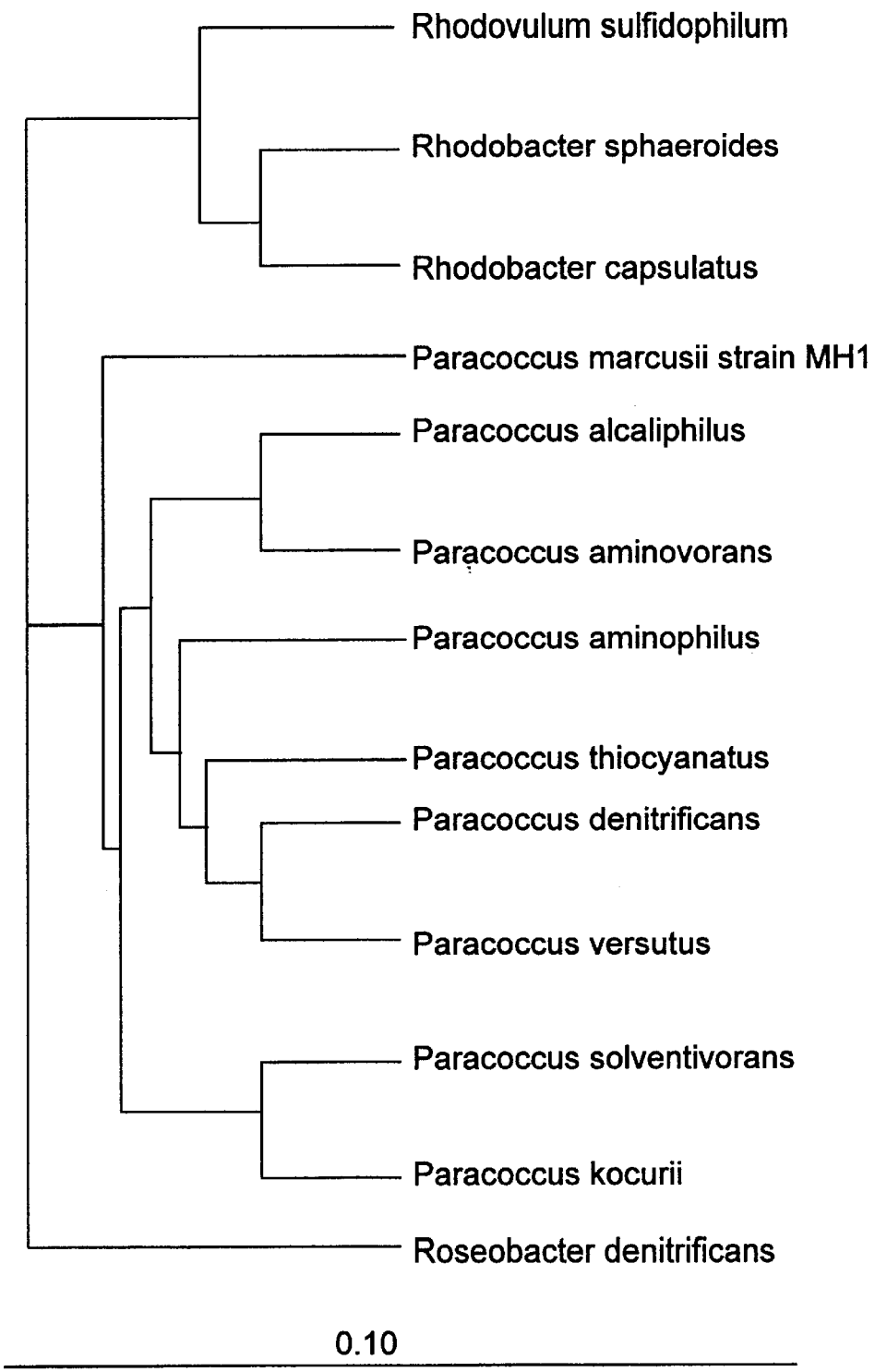
FIG. 5 shows a dendrogram indicating the position of *Paracoccus marcusii* strain MH1 among the representatives of the genus Paracoccus and related species within the α-branch of the Proteobacteria, wherein the scale bar indicates 10 nucleotide substitutions per 100 nucleotides.

Approximately 95% of the 16S rRNA gene sequence of strain MH1 was determined by direct sequencing of PCR-amplified 16S rDNA. Based solely on 16S rRNA phylogenetic, (see similarity values in Table 1 below and the phylogenetic tree of FIG. 5) it could be determined that strain MH1 is most similar to the genus Paracoccus within the Rhodobacter group of the α-subdivision of the Proteobacteria. The highest 16S rRNA gene similarity values exist between strain MH1 and *Paracoccus alcaliphilus* JCM $7364^T$ (96.3%) or *Paracoccus aminophilus* JCOM $7686^T$ (96.2%). Since strain MH1 is only remotely related to the other species of the genus Paracoccus (% sequence similarities between 96.3–93.6), and since it produces and secretes carotenoids it may be regarded as a member of a novel genus reported herein for the first time.

Table 1 presents a similarity matrix of the 16S rDNA gene sequences for *Paracoccus marcusii* and related Paracoccus species. The 16S rRNA gene similarity values were calculated by pairwise comparison of the sequences within the alignment.

The phenotypic properties of strain MH 1 all fit within the framework of the emended description of the genus Paracoccus [Katayama, Y., A. Hiraishi, and H. Kuraishi. 1995. *Paracoccus thiocyanatus* sp. nov., a new species of thiocyanate-utilizing facultative chemolithotroph, and transfer of *Thiobacillus versutus* to the genus Paracoccus as *Paracoccus versutus* comb. nov. with emendation of the genus. Microbiology 141:1469–1477]. We propose to name Paracoccus strain MH1, *Paracoccus marcusii*, in honor of the late Prof. Menashe Marcus, a pioneer of genetic research in Israel.

TABLE 1

| | 1 | 2 | 3 | 4 | 5 | 6 | 7 | 8 | 9 | 10 | 11 | 12 | 13 |
|---|---|---|---|---|---|---|---|---|---|---|---|---|---|
| 1. *Paracoccus marcusii* DSM $11574^T$ | — | | | | | | | | | | | | |
| 2. *Paracoccus alcaliphilus* JCM $7364^T$ | 96.3 | — | | | | | | | | | | | |
| 3. *Paracoccus aminophilus* JCM $7686^T$ | 96.2 | 96.4 | — | | | | | | | | | | |
| 4. *Paracoccus aminovorans* JCM $7685^T$ | 95.5 | 96.9 | 96.3 | — | | | | | | | | | |
| 5. *Paracoccus thiocyanatus* IAM $12816^T$ | 95.4 | 96.8 | 97.1 | 96.8 | — | | | | | | | | |
| 6. *Paracoccus solventivorans* DSM $6637^T$ | 95.1 | 95.7 | 95.7 | 95.4 | 96.2 | — | | | | | | | |
| 7. *Paracoccus kocurii* JCM $7684^T$ | 94.4 | 95.8 | 94.9 | 94.7 | 96.0 | 96.7 | — | | | | | | |
| 8. *Paracoccus denitrificans* LMG $4218^T$ | 93.3 | 95.8 | 96.3 | 96.0 | 96.8 | 95.8 | 95.5 | — | | | | | |
| 9. *Paracoccus versutus* IAM $12814^T$ | 93.6 | 95.4 | 96.0 | 96.6 | 96.5 | 95.7 | 95.4 | 99.3 | — | | | | |
| 10. *Rhodobacter sphaeroides* ATCC $17023^T$ | 92.8 | 92.5 | 92.9 | 92.5 | 92.8 | 92.9 | 93.3 | 93.0 | 92.5 | — | | | |
| 11. *Rhodobacter capsulatus* ATCC $17015^T$ | 92.5 | 91.7 | 92.8 | 93.2 | 92.5 | 92.0 | 92.2 | 93.0 | 93.4 | 95.6 | — | | |
| 12. *Rhodovulum sulfidophilum* DSM $1374^T$ | 92.0 | 92.2 | 91.4 | 91.6 | 90.9 | 92.2 | 92.2 | 91.8 | 91.3 | 93.0 | 93.4 | — | |
| 13. *Roseobacter denitrificans* ATCC $33942^T$ | 90.9 | 91.3 | 91.9 | 91.7 | 91.1 | 91.1 | 90.3 | 91.1 | 90.8 | 90.7 | 90.1 | 89.9 | — |

Hiraishi, and H. Kuraishi. 1995. *Paracoccus thiocyanatus* sp. nov., a new species of thiocyanate-utilizing facultative chemolithotroph, and transfer of *Thiobacillus versutus* to the Table 2 below summarizes a comparison of the properties of *Paracoccus marcusii* strain MH1 with the previously described representatives of the genus Paracoccus.

TABLE 2

| Characteristics | 1 | 2 | 3 | 4 | 5 | 6 | 7 | 8 | 9 |
|---|---|---|---|---|---|---|---|---|---|
| Motility | − | − | − | +/− | − | − | − | − | − |
| Growth in 6% NaCl | w | − | NR | NR | − | − | − | − | − |
| Utilization of glycerol | + | +/− | − | + | w | w | + | + | − |
| Utilization of glucose | + | + | − | + | − | − | − | − | − |
| Utilization of mannitol | + | + | + | + | − | + | − | + | − |
| Utilization of fructose | + | + | + | + | − | + | − | + | − |
| $NO_3^-$ reduced to $NO_2^-$ | − | + | + | + | + | + | + | + | + |
| $NO_2^-$ reduced to $N_2$ | − | + | + | + | + | − | − | − | + |
| Growth on formate | + | + | w | + | + | − | − | − | − |
| Growth on methanol | − | +/− | − | w | − | + | − | − | − |
| Growth on methylamine | − | +/− | NR | NR | + | +/− | + | + | − |
| Growth on trimethylamine | − | − | NR | NR | + | − | + | + | − |
| Yellow pigment | + | − | + | − | − | − | − | − | − |
| Carotenoids production | + | − | −* | − | − | − | − | − | − |
| Mol % G + C of DNA | 66 | 68 | 66.5 | 67–68 | 71 | 64–6 | 63 | 67–6 | 68.5–70 |

1— *P. marcusii*, 2— *P. denitrificans*, 3— *P. thiocyanatus*, 4— *P. versutus*, 5— *P. kocurii*, 6— *P. alcaliphilus*, 7— *P. aminophilus*, 8— *P. aminovorans*, 9— *P. solventivorans*. w = weak reaction. ± = variable. NR = not reported. *P. thiocyanatus* was obtained from the IAM Culture Collection, Bacterial Section, Institute of Molecular and Cellular Biosciences, The University of Tokyo, Yayoi, Bunko-ku, Tokyo, 113, Japan, and was examined for carotenoids production due to its yellow pigmentation. No carotenoids were detectable using any of the approaches listed under the methods section above.

Example 5

Carotenoids Synthesis by *Paracoccus marcusii*

The following carotenoids were recovered from cells, medium and/or vesicles of *Paracoccus marcusii* strain MH1 grown as described under the methods section above.

β-carotene: $R_F$=0.98 (TLC 1), $R_F$=0.98 (TLC 2) inseparable from authentic β-carotene upon TLC and HPLC. Vis $\lambda_{max}$. nm (426) 453 and 477 (acetone); (426) 449 and 476 (diethyl ether), %III/II=22. MS m/z 536 $[M]^+$, 444 $[M-92]^+$, 430 $[M-106]^+$.

Echinenone: $R_F$=0.92 (TLC 1), $R_F$=0.94 (TLC 2) inseparable from authentic echinenone upon TLC and HPLC. Vis $\lambda_{max}$. nm 460 (acetone); 457 (diethyl ether), %III/II=0. MS m/z 550 $[M]^+$, 458 $[M-92]^+$.

β-cryptoxanthin: $R_F$=0.84 (TLC 1), $R_F$=0.80 (TLC 2) no standard available. Vis $\lambda_{max}$. nm (426) 454 and 478 (acetone); (423) 453 and 477 (diethyl ether), %III/II=27. Insufficient amount for MS.

Canthaxanthin: $R_F$=0.71 (TLC 1), $R_F$=0.65 (TLC 2) inseparable from authentic canthaxanthin upon TLC and HPLC. Vis $\lambda_{max}$. nm 470 (acetone), %III/II=0. MS m/z 564 $[M]^+$, 472 $[M-92]^+$.

Adonirubin: $R_F$=0.65 (TLC 1), $R_F$=0.58 (TLC 2) inseparable from authentic adonirubin upon TLC and HPLC. Vis $\lambda_{max}$. nm 473 (acetone); 465 (diethyl ether), %III/II=0. MS m/z 580 $[M]^+$, 488 $[M-92]^+$.

Cis-Adonixanthin: $R_F$=0.57 (TLC 1), $R_F$=0.51 (TLC 2) no standard available. Vis $\lambda_{max}$. nm 465 (acetone), %III/II=0. MS m/z 582 $[M]^+$, 580 $[M-2]^+$, 564 $[M-18]^+$, 490 $[M-92]^+$.

Adonixanthin: $R_F$=0.59 (TLC 1), $R_F$=0.51 (TLC 2) no standard available. Vis $\lambda_{max}$. nm 465 (acetone); 463 (diethyl ether), %III/II=0. MS m/z 582 $[M]^+$, 580 $[M-2]^+$, 564 $[M-18]^+$, 509 $[M-73]^+$, 490 $[M-92]^+$.

Astaxanthin: $R_F$=0.55 (TLC 1), $R_F$=0.48 (TLC 2) inseparable from authentic astaxanthin upon TLC and HPLC. Vis $\lambda_{max}$. nm 474 (acetone), (428) 451 478 after $NaBH_4$ reduction; 470 (diethyl ether), %III/II=0. MS m/z 596 $[M]^+$, 578 $[M-16]^+$, 564 $[M-32]^+$, 490 $[M-106]^+$.

Zeaxanthin: $R_F$=0.43 (TLC 1), $R_F$=0.43 (TLC 2) inseparable from authentic zeaxanthin upon TLC and HPLC. Vis $\lambda_{max}$. nm (426) 453 and 477 (acetone); (426) 449 and 476 (diethyl ether), %III/II=45. Insufficient amount for MS.

Table 3 presents the total content and distribution of the above carotenoids in *P. marcusii* cells.

TABLE 3

| Carotenoid | % of total carotenoid |
|---|---|
| Beta-Carotene | 5.2 |
| Beta-Cryptoxanthin | 0.8 |
| Echinenone | 7.0 |
| Zeaxanthin | 1.9 |
| 3'-Hydroxyechinenone | 14.6 |
| Hydroxyechinenone | 4.6 |
| Canthaxanthin | 9.5 |
| Adonirubin | 9.4 |
| Adonixanthin | 33.2 |
| Cis-Adonixanthin | 2.3 |
| Astaxanthin | 11.5 |
| Total Carotenoids mg/l culture | 1.5 |
| Total carotenoid % of dry wt. | 0.2 |

Example 6

Transmission Electron Microscopy of *Paracoccus marcusii*

The phenomenon of carotenoid excretion into the growth medium by cells of *P. marcusii* strain MH1 was investigated by the use of transmission electron microscopy. The possibility of the involvement of specific cellular structures in this mechanism, and at which stage of cellular development such structures appeared was determined.

Figure 6A:
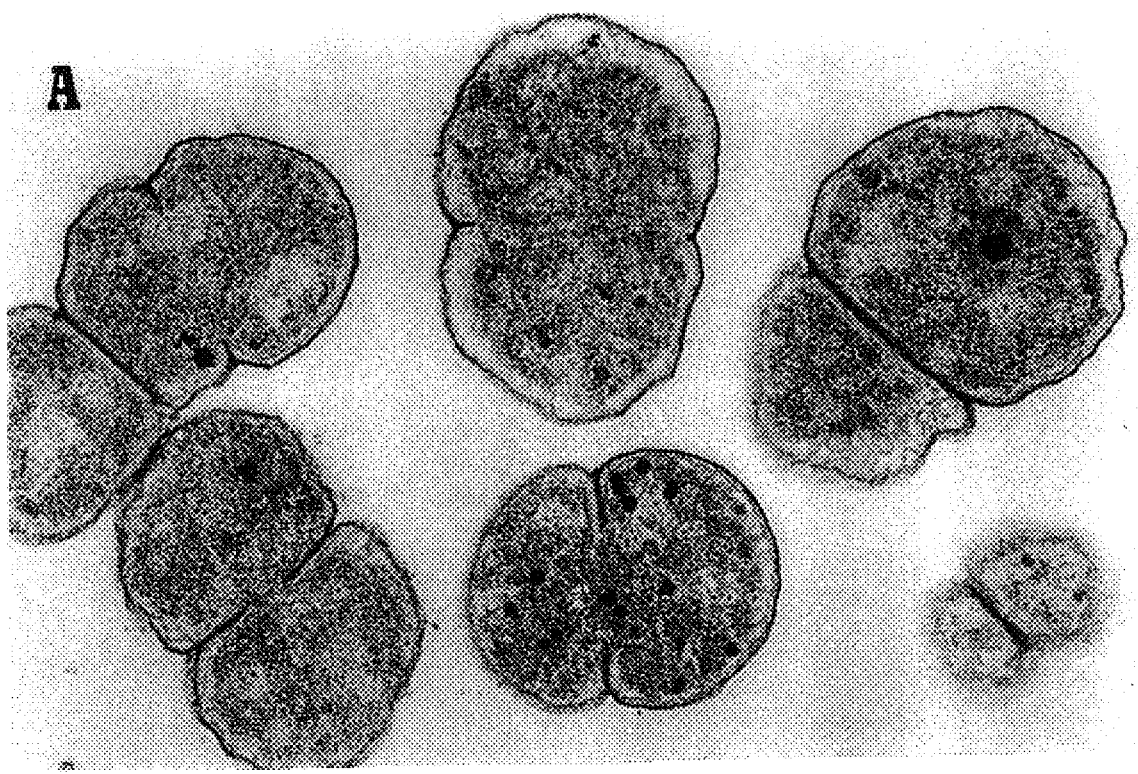
FIGS. 6a–d are electron micrographs of *Paracoccus marcusii* strain MH1 during mid-logarithmic stage of growth, late-logarithmic stage of growth, early stationary stage of growth and late stationary stage of growth, respectively (magnification×40,000).
Figure 6B:
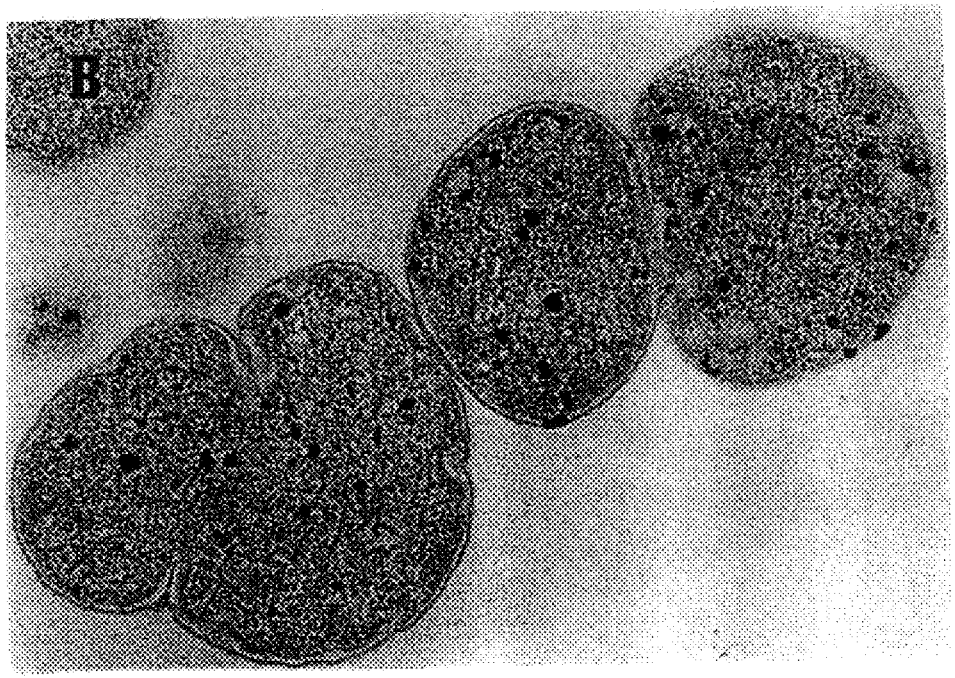

FIG. 6a shows typical cells during the mid-logarithmic stage of growth in a suspension culture at cell density of $OD_{600}$ of 0.7. A small number of lipophillic globules (vesicles) are clearly visible within the dividing cells. The number of these globules varies considerably from cell to cell according to the position of the section. As the culture ages the number of globules increases, whilst numerous smaller globules also become apparent within the cells. This can be observed in FIG. 6b and, which shows cells at the late-logarithmic stage of growth at cell density of $OD_{600}$ of 1.3. The large globules are observed to migrate to the periphery of the cell and move into the periplasmic space.

Figure 6C:
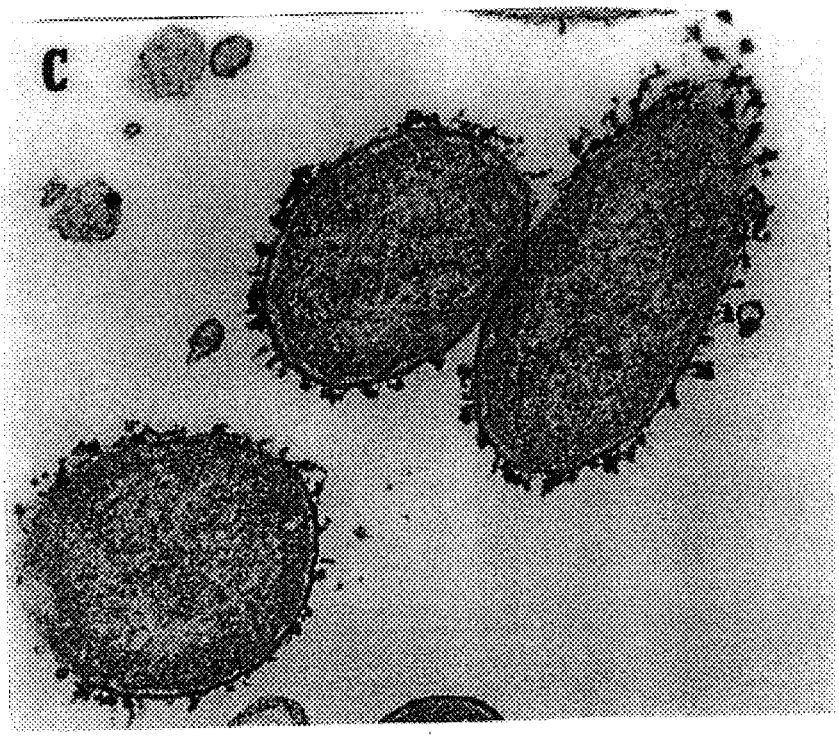
Figure 6D:
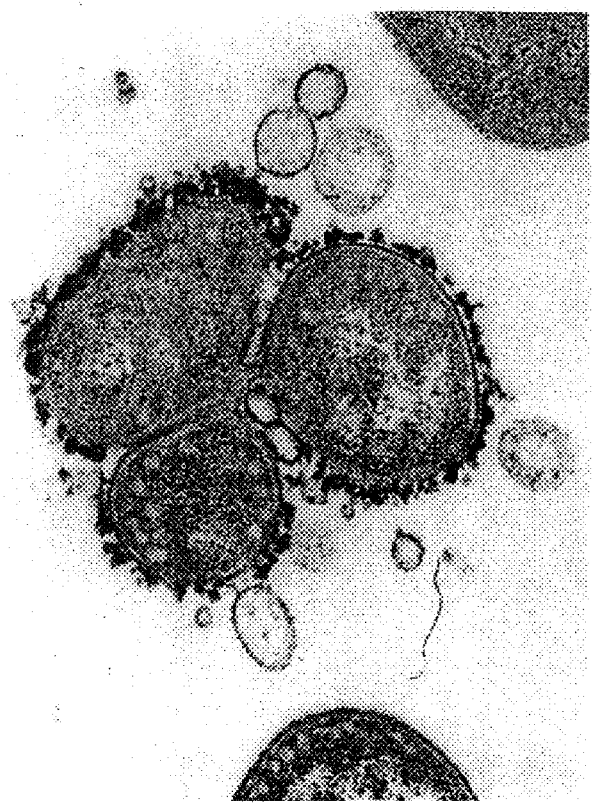

The globules then move across the cell wall into small circular vesicles that emerge outside the cell. Blebbing of these globules from the cell wall results in the formation of darkly stained, hence lipophillic, vesicles which initially remain attached to the surface of the cell. This phenomena is clearly distinguishable in FIG. 6c. In later stages the surface of the cells become covered by these vesicles, as seen in FIG. 6d, and form a complete separate entity, which is eventually released into the growth medium.

Figure 7:
FIG. 7. is an electron micrograph of isolated vesicles secreted by *Paracoccus marcusii* strain MH1 (magnification×200,000).

Analysis of the medium, taken from a suspension culture at the stationary growth phase, cell density of $OD_{600}$ of 1.58, shows that these vesicles exist as separate entities in the medium (FIG. 7). Carotenoid analysis of these vesicles showed that they contain mainly adonixanthin (Table 4 below).

The carotenoid accumulation in the cells during the aging of the cell culture completely correlates with the appearance of the darkly stained, lipophyllic globules seen within the bacterial cells. Moreover, the appearance of released vesicles in the liquid growth medium correlates with the appearance of carotenoids outside the cells. Finally, in a purified vesicle preparation that was isolated by ultracentrifugation from the growth medium one finds mainly keto-carotenoids (see table 4).

It is the excretion of these carotenoid containing vesicles which is responsible for the color change of the growth medium observed during the cultivation of *P. marcusii* cultures. It was further determined quantitatively that substantially all of the secreted, i.e., medium associated, caratenoids are within the vesicle fraction.

TABLE 4

Carotenoid Composition of *P. marcusii* Culture

| Carotenoid | % of total carotenoid | |
|---|---|---|
| | Cells | Media |
| β-carotene | 5.2 | — |
| β-cryptoxanthin | 0.8 | — |
| Echinenone | 7.0 | — |

TABLE 4-continued

Carotenoid Composition of *P. marcusii* Culture

| Carotenoid | % of total carotenoid | |
|---|---|---|
| | Cells | Media |
| Zeaxanthin | 1.9 | — |
| 3'-Hydroxyechinenone | 14.6 | 10.9 |
| Hydroxyechinenone | 4.6 | — |
| Canthaxanthin | 9.5 | — |
| Adonirubin | 9.4 | — |
| Adonixanthin | 33.2 | 78.1 |
| Cis-Adonixanthin | 2.3 | 3.9 |
| Astaxanthin | 11.5 | 7.1 |
| Total carotenoids mg/l culture | 2.1 | |
| Total carotenoid of cells mg/l | 1.5 | |
| Total carotenoid % of dry wt. of cells | 0.2 | |
| Total carotenoid of media mg/l | 0.6 | |

Example 7

Determining the chirality configuration of astaxanthin produced by *Paracoccus marcusii*

The chirality configurations of astaxanthin produced by *Paracoccus marcusii* cells was determined by HPLC of the derived diastereoisomeric camphanates of the astaxanthin [Renstrom B., Borch G., Skulberg M. and Liaaen-Jensen S. (1981) Optical purity of (3S,3S')-astaxanthin from *Haematococcus pluvialis*. Phytochem 20: 2561–2565]. The analysis proved that *Paracoccus marcusii* synthesize pure (3S, 3'S) astaxanthin.

Thus, the present invention successfully addresses the shortcomings of the presently known configurations by providing a novel bacterial species secreting carotenoids, and in particular (3S,3'S) astaxanthin, which makes the process of carotenoids purification simpler.

While the invention has been described with respect to a limited number of embodiments, it will be appreciated that many variations, modifications and other applications of the invention may be made.

What is claimed is:

1. A process for production of at least one carotenoid pigment comprising the steps of:
   (a) culturing a bacterial species of the genus Paracoccus, as determined by 16S ribosomal RNA gene homology, said bacterial species producing the at least one carotenoid pitment, in a nutrient medium including sources of carbon, nitrogen and inorganic substances; and
   (b) recovering an individual carotenoid pigment or a mixture of carotenoid pigments.

2. The process of claim 1, wherein said species secretes at least one carotenoid during its life cycle and therefore said recovering is from said medium.

3. The process of claim 1, wherein said species at least partially accumulates at least one carotenoid during its life cycle and therefore said recovering is from cells of said species.

4. The process of claim 1, wherein said species is *Paracoccus marcusii* strain MH1, which has been deposited with the Deutsche Sammlung von Mikoorganismen und Zellkulturen as strain DSM 11574$^T$.

5. A process for production of at least one carotenoid pigment comprising the steps of:
   (a) providing a bacterial species of the genus Paracoccus, as determined by 16S ribosomal RNA gene homology, said bacterial species producing the at least one carotenoid pigment;
   (b) providing said species with growing conditions for production of at least one carotenoid pigment; and
   (c) extracting at least one carotenoid pigment or a mixture of carotenoid pigments.

6. The process of claim 5, wherein said species secretes at least one carotenoid during its life cycle and therefore said recovering is from said medium.

7. The process of claim 5, wherein said species at least partially accumulates at least one carotenoid during its life cycle and therefore said recovering is from cells of said species.

8. The process of claim 5, wherein said species is *Paracoccus marcusii* strain MH1, which has been deposited with the Deutsche Sammlung von Mikoorganismen und Zellkulturen as strain DSM 11574$^T$.

9. The process of claim 1, wherein said at least one carotenoid pigment is selected from the group consisting of β-carotene, echinenone, β-cryptoxanthin, canthaxanthin, adonirubin, cis-adonixanthin, adonixanthin, astaxanthin and zeaxanthin.

10. The process of claim 5, wherein said at least one carotenoid pigment is selected from the group consisting of β-carotene, echinenone, β-cryptoxanthin, canthaxanthin, adonirubin, cis-adonixanthin, adonixanthin, astaxanthin and zeaxanthin.

11. A process for production of least one carotenoid pigment comprising the steps of:

(a) culturing a bacterial species of the genus Paracoccus as determined by 16 S ribosomal RNA gene homology, said bacterial species secreting carotenoid containing vesicles, in a nutrient medium including sources of carbon, nitrogen and inorganic substances; and (b) recovering an individual carotenoid pigment or a mixture of carotenoid pigments.

12. The process of claim 11, wherein said recovering is from said vesicles.

13. The process of claim 11, wherein said species is *Paracoccus marcusii* strain MH1, which has been deposited with the Deutsche Sammlung von Mikoorganismen und Zellkulturen as strain DSM $11574^T$.

14. The process of claim 11, wherein said at least one carotenoid pigment is selected from the group consisting of β-carotene, echinenone, β-cryptoxanthin, canthaxanthin, adonirubin, cis-adonixanthin, adonixanthin, astaxanthin and zeaxanthin.

* * * * *

SEQUENCE LISTING (1) GENERAL INFORMATION:

(iii) NUMBER OF SEQUENCES:1

(2) INFORMATION FOR SEQ ID NO:1:

(i) SEQUENCE CHARACTERISTICS:
      (A) LENGTH:1430

(B) TYPE:nucleic acid (C) STRANDEDNESS:double (D) TOPOLOGY:linear (xi) SEQUENCE DESCRIPTION: SEQ ID NO:1:

```
CAGAACGAAC GCUGGCGGCA GGCUUAACAC AUGCAAGUCG AGCGAGACCU         50

UCGGGUCUAG CGGCGGACGG GUGAGUAACG CGUGGGAACG UGCCCUUCUC        100
```

-continued

| | |
|---|---|
| UACGGAAUAG CCCCGGGAAA CUGGGAGUAA UACCGUAUAC GCCCUUUGGG | 150 |
| GGAAAGAUUU AUCGGAGAAG GAUCGGCCCG CGUUGGAUUA GGUAGUUGGU | 200 |
| GGGGUAAUGG CCCACCAAGC CGACGAUCCA UAGCUGGUUU GAGAGGAUGA | 250 |
| UCAGCCACAC UGGGACUGAG ACACGGCCCA GACUCCUACG GGAGGCAGCA | 300 |
| GUGGGGAAUC UUAGACAAUG GGGGCAACCC UGAUCUAGCC AUGCCGCGUG | 350 |
| AGUGAUGAAG GCCUUAGGGU UGUAAAGCUC UUUCAGCUGG GAAGAUAAUG | 400 |
| ACGGUACCAG CAGAAGAAGC CCCGGCUAAC UCCGUGCCAG CAGCCGCGGU | 450 |
| AAUACGGAGG GGGCUAGCGU UGUUCGGAAU UACUGGGCGU AAAGCGCACG | 500 |
| UAGGCGGACU GGAAAGUCAG AGGUGAAAUC CCAGGGCUCA ACCUUGGAAC | 550 |
| UGCCUUUGAA ACUAUCAGUC UGGAGUUCGA GAGAGGUGAG UGGAAUUCCG | 600 |
| AGUGUAGAGG UGAAAUUCGU AGAUAUUCGG AGGAACACCA GUGGCGAAGG | 650 |
| CGGCUCACUG GCUCGAUACU GACGCUGAGG UGCGAAAGCG UGGGGAGCAA | 700 |
| ACAGGAUUAG AUACCCUGGU AGUCCACGCC GUAAACGAUG AAUGCCAGAC | 750 |
| GUCGGCAAGC AUGCUUGUCG GUGUCACACC UAACGGAUUA AGCAUUCCGC | 800 |
| CUGGGGAGUA CGGUCGCAAG AUUAAAACUC AAAGGAAUUG ACGGGGCCC | 850 |
| GCACAAGCGG UGGAGCAUGU GGUUUAAUUC GAAGCAACGC GCAGAACCUU | 900 |
| ACCAACCCUU GACAUGGCAG GACCGCUGGA GAGAUUCAGC UUUCUCGUAA | 950 |
| GAGACCUGCA CACAGGUGCU GCAUGGCUGU CGUCAGCUCG UGUCGUGAGA | 1000 |
| UGUUCGGUUA AGUCCGGCAA CGAGCGCAAC CCACGUCCCU AGUUGCCAGC | 1050 |
| AUUCAGUUGG GCACUCUAUG GAAACUGCCG AUGAUAAGUC GGAGGAAGGU | 1100 |
| GUGGAUGACG UCAAGUCCUC AUGGCCCUUA CGGGUUGGGC UACACACGUG | 1150 |
| CUACAAUGGU GGUGACAGUG GGUUAAUCCC CAAAAGCCAU CUCAGUUCGG | 1200 |
| AUUGUCCUCU GCAACUCGAG GGCAUGAAGU UGGAAUCGCU AGUAAUCGCG | 1250 |
| GAACAGCAUG CCGCGGUGAA UACGUUCCCG GGCCUUGUAC ACACCGCCCG | 1300 |
| UCACACCAUG GGAGUUGGUU CUACCCGACG ACGCUGCGCU AACCUUCGGG | 1350 |
| GGGCAGGCGG CCACGGUAGG AUCAGCGACU GGGGUGAAGU CGUAACAAGG | 1400 |
| UAGCCGUAGG GGAACCUGCG GCUGGAUCAC | 1430 |